(12) United States Patent
Miller et al.

(10) Patent No.: US 12,245,753 B2
(45) Date of Patent: Mar. 11, 2025

(54) CONDUCTIVE OPTICAL ELEMENT

(71) Applicant: GI SCIENTIFIC, LLC, Arlington, VA (US)

(72) Inventors: Scott Miller, Arlington, VA (US); Frank Carter, Wormleysburg, PA (US); Adnan Merchant, Fremont, CA (US); Carl Gauger, Kansas City, MO (US)

(73) Assignee: GI SCIENTIFIC, LLC, Arlington, VA (US)

( * ) Notice: Subject to any disclaimer, the term of this patent is extended or adjusted under 35 U.S.C. 154(b) by 0 days.

(21) Appl. No.: 18/137,384

(22) Filed: Apr. 20, 2023

(65) Prior Publication Data

US 2023/0255463 A1    Aug. 17, 2023

Related U.S. Application Data

(63) Continuation of application No. 16/776,168, filed on Jan. 29, 2020, now Pat. No. 11,666,208, which is a
(Continued)

(51) Int. Cl.
*A61B 1/12* (2006.01)
*A61B 1/00* (2006.01)
(Continued)

(52) U.S. Cl.
CPC .......... *A61B 1/128* (2013.01); *A61B 1/00027* (2013.01); *A61B 1/00087* (2013.01);
(Continued)

(58) Field of Classification Search
CPC . A61B 1/00087; A61B 1/00096; A61B 1/127; A61B 1/128; A61B 1/00027
See application file for complete search history.

(56) References Cited

U.S. PATENT DOCUMENTS 3,774,614 A   11/1973  Cook
3,858,577 A   1/1975   Bass et al.
(Continued)

FOREIGN PATENT DOCUMENTS

CN    1692872 A    11/2011
DE    3532609 A    3/1987
(Continued)

OTHER PUBLICATIONS

European Examination Report for EP Appl. No. 15843356.5 dated May 20, 2019, 7 pages.
(Continued)

*Primary Examiner* — Aaron B Fairchild
(74) *Attorney, Agent, or Firm* — Farber LLC

(57) ABSTRACT

A device having an optical element with a conductive coating. The device may include an optical element, a conductive material and at least one connector. The conductive material is disposed on at least a portion of the optical element. The optical element, for example, may be an object lens of an endoscope or an optical coupler. The connectors (acting as terminal(s)) are capable of providing energy (such as electrical energy) to the conductive material. In one aspect, the conductive material is an optically transparent material. Advantageously, the device may allow visualization of an object—such as body tissue or other matter—concurrent with the application of energy to the object via the conductive coating. This allows the user to observe the alteration of tissue and other matter in real time as the energy is delivered.

16 Claims, 12 Drawing Sheets

Related U.S. Application Data continuation of application No. 14/728,812, filed on Jun. 2, 2015, now Pat. No. 10,548,467.

(51) Int. Cl.
*A61B 18/08* (2006.01)
*A61B 18/14* (2006.01)
*A61N 7/02* (2006.01)
*A61B 18/00* (2006.01)
*A61B 18/18* (2006.01)
*A61N 7/00* (2006.01)

(52) U.S. Cl.
CPC .......... *A61B 1/00096* (2013.01); *A61B 1/127* (2013.01); *A61B 18/082* (2013.01); *A61B 18/14* (2013.01); *A61B 18/1492* (2013.01); *A61N 7/022* (2013.01); *A61B 2018/00059* (2013.01); *A61B 2018/00583* (2013.01); *A61B 2018/00595* (2013.01); *A61B 2018/00607* (2013.01); *A61B 2018/00982* (2013.01); *A61B 2018/1405* (2013.01); *A61B 2018/147* (2013.01); *A61B 18/1815* (2013.01); *A61N 2007/0043* (2013.01)

(56) References Cited

U.S. PATENT DOCUMENTS

| | | | |
|---|---|---|---|
| 4,090,501 A | 5/1978 | Chaitin |
| 4,201,199 A | 5/1980 | Smith |
| 4,207,872 A | 6/1980 | Meiri et al. |
| 4,340,811 A | 7/1982 | Yamashita et al. |
| 4,681,093 A | 7/1987 | Ono et al. |
| 4,696,544 A | 9/1987 | Costella |
| 4,744,620 A | 5/1988 | Ueno et al. |
| 4,779,611 A | 10/1988 | Grooters et al. |
| 4,805,598 A | 2/1989 | Ueda |
| 4,878,725 A | 11/1989 | Hessel et al. |
| 4,881,810 A | 11/1989 | Hasegawa |
| 4,888,243 A | 12/1989 | Jonas et al. |
| 4,967,732 A | 11/1990 | Inoue |
| 5,040,715 A | 8/1991 | Green et al. |
| 5,050,585 A | 9/1991 | Takahashi |
| 5,080,660 A | 1/1992 | Buelna |
| 5,104,025 A | 4/1992 | Main et al. |
| 5,137,198 A | 8/1992 | Nobis et al. |
| 5,201,900 A | 4/1993 | Nardella |
| 5,205,459 A | 4/1993 | Brinkerhoff et al. |
| 5,237,984 A | 8/1993 | Williams, III et al. |
| 5,271,379 A | 12/1993 | Phan et al. |
| 5,326,013 A | 7/1994 | Green et al. |
| 5,329,935 A | 7/1994 | Takahashi |
| 5,337,734 A | 8/1994 | Saab |
| 5,342,388 A | 8/1994 | Toller |
| 5,413,052 A | 5/1995 | Breezer et al. |
| 5,413,268 A | 5/1995 | Green et al. |
| 5,443,781 A | 8/1995 | Saab |
| 5,448,990 A | 9/1995 | De Faria-Correa |
| 5,460,168 A | 10/1995 | Masubuchi et al. |
| 5,476,206 A | 12/1995 | Green et al. |
| 5,536,236 A | 7/1996 | Yabe et al. |
| 5,555,129 A | 9/1996 | Konno et al. |
| 5,575,291 A | 11/1996 | Hayakawa et al. |
| 5,605,532 A | 2/1997 | Schermerhorn |
| 5,632,717 A | 5/1997 | Yoon |
| 5,657,921 A | 8/1997 | Young et al. |
| 5,662,258 A | 9/1997 | Knodel et al. |
| 5,674,181 A | 10/1997 | Lida |
| 5,707,342 A | 1/1998 | Tanaka |
| 5,725,474 A | 3/1998 | Yasui et al. |
| 5,725,475 A | 3/1998 | Yasui et al. |
| 5,738,629 A | 4/1998 | Moll et al. |
| 5,743,851 A | 4/1998 | Moll et al. |
| 5,771,327 A | 6/1998 | Bar-Or et al. |
| 5,788,628 A | 8/1998 | Matsuno et al. |
| 5,808,813 A | 9/1998 | Lucey et al. |
| 5,840,014 A | 11/1998 | Miyano et al. |
| 5,860,913 A | 1/1999 | Yamaya et al. |
| 5,897,487 A | 4/1999 | Ouchi |
| 5,916,148 A | 6/1999 | Tsuyuki |
| 6,059,719 A | 5/2000 | Yamamoto et al. |
| 6,131,789 A | 10/2000 | Schulze et al. |
| 6,217,509 B1 | 4/2001 | Foley et al. |
| 6,250,532 B1 | 6/2001 | Green et al. |
| 6,277,065 B1 | 8/2001 | Donofrio |
| 6,283,951 B1 | 9/2001 | Flaherty et al. |
| 6,293,907 B1 | 9/2001 | Axon et al. |
| 6,306,081 B1 | 10/2001 | Ishikawa et al. |
| 6,409,725 B1 | 6/2002 | Khandkar et al. |
| 6,416,462 B1 | 7/2002 | Tovey et al. |
| 6,673,091 B1 | 1/2004 | Shaffer et al. |
| 6,699,180 B2 | 3/2004 | Kobayashi |
| 6,712,524 B2 | 3/2004 | Beatty et al. |
| 6,723,350 B2 | 4/2004 | Burrell et al. |
| 6,733,440 B2 | 5/2004 | Ailinger et al. |
| 6,770,069 B1 | 8/2004 | Hobart et al. |
| 6,792,837 B2 | 9/2004 | Battistone |
| 6,855,108 B2 | 2/2005 | Ishibiki et al. |
| 6,866,627 B2 | 3/2005 | Nozue |
| 6,934,093 B2 | 8/2005 | Kislev et al. |
| 6,981,628 B2 | 1/2006 | Wales |
| 6,988,650 B2 | 1/2006 | Schwemberger et al. |
| 7,033,317 B2 | 4/2006 | Pruitt |
| 7,046,439 B2 | 5/2006 | Kaminsky et al. |
| 7,087,012 B2 | 8/2006 | Ishibiki |
| 7,112,195 B2 | 9/2006 | Boll et al. |
| 7,205,339 B2 | 4/2007 | Muratoglu |
| 7,235,592 B2 | 6/2007 | Muratoglu et al. |
| 7,238,153 B2 | 7/2007 | Moriyama |
| 7,245,813 B2 | 7/2007 | Brown et al. |
| 7,464,847 B2 | 12/2008 | Viola et al. |
| 7,537,561 B2 | 5/2009 | Yamaya et al. |
| 7,553,278 B2 | 6/2009 | Kucklick |
| 7,554,743 B2 | 6/2009 | Jiang et al. |
| 7,566,993 B2 | 7/2009 | May |
| 7,621,868 B2 | 11/2009 | Breidenthal et al. |
| 7,819,872 B2 | 10/2010 | Johnson et al. |
| 7,977,255 B1 | 7/2011 | Scheer et al. |
| 8,180,423 B2 | 5/2012 | Mang et al. |
| 8,905,921 B2 | 12/2014 | Titus |
| 8,915,931 B2 | 12/2014 | Boudreaux et al. |
| 9,459,442 B2 | 10/2016 | Miller |
| 9,709,795 B2 | 7/2017 | Miller |
| 10,101,574 B2 | 10/2018 | Miller |
| 2002/0035311 A1 | 3/2002 | Ouchi |
| 2002/0065515 A1 | 5/2002 | Falwell et al. |
| 2002/0133148 A1 | 9/2002 | Daniel et al. |
| 2003/0181900 A1 | 9/2003 | Long |
| 2004/0157073 A1 | 8/2004 | Burrell et al. |
| 2004/0249246 A1 | 12/2004 | Campos |
| 2004/0263613 A1 | 12/2004 | Morita |
| 2004/0267092 A1 | 12/2004 | Ishibiki |
| 2005/0043589 A1 | 2/2005 | Pruitt |
| 2005/0080411 A1 | 4/2005 | Ouchi |
| 2005/0131279 A1 | 6/2005 | Boulais et al. |
| 2005/0197530 A1 | 9/2005 | Wallace et al. |
| 2006/0030844 A1 | 2/2006 | Knight et al. |
| 2006/0084839 A1 | 4/2006 | Mourlas et al. |
| 2006/0173241 A1 | 8/2006 | Ouchi et al. |
| 2006/0200176 A1 | 9/2006 | Matsuno et al. |
| 2006/0229662 A1 | 10/2006 | Finkielsztein et al. |
| 2006/0270900 A1 | 11/2006 | Chin et al. |
| 2007/0038043 A1 | 2/2007 | Gelikonov et al. |
| 2007/0066869 A1 | 3/2007 | Hoffman |
| 2007/0066870 A1 | 3/2007 | Ohashi et al. |
| 2007/0073108 A1 | 3/2007 | Takahashi |
| 2007/0208219 A1 | 9/2007 | Carter |
| 2007/0239620 A1 | 10/2007 | Schwartz et al. |
| 2007/0260117 A1 | 11/2007 | Zwolinski et al. |
| 2007/0282256 A1 | 12/2007 | Hu et al. |
| 2007/0293888 A1 | 12/2007 | Harren et al. |
| 2008/0021268 A1 | 1/2008 | Shoroji et al. |
| 2008/0021269 A1 | 1/2008 | Tinkham et al. |
| 2008/0033246 A1 | 2/2008 | Matsui et al. |

(56) References Cited

U.S. PATENT DOCUMENTS

| | | |
|---|---|---|
| 2008/0139885 A1 | 6/2008 | Knapp |
| 2008/0188874 A1 | 8/2008 | Henderson |
| 2008/0262295 A1 | 10/2008 | Kendale et al. |
| 2008/0306335 A1 | 12/2008 | Lau et al. |
| 2009/0048483 A1 | 2/2009 | Yamamoto |
| 2009/0048486 A1 | 2/2009 | Surti |
| 2009/0062790 A1 | 3/2009 | Malchano et al. |
| 2009/0098409 A1 | 4/2009 | Yamada et al. |
| 2009/0143643 A1 | 6/2009 | Weitzner et al. |
| 2009/0156898 A1 | 6/2009 | Ichimura |
| 2009/0254164 A1 | 10/2009 | Johnson et al. |
| 2009/0315989 A1 | 12/2009 | Adelson |
| 2009/0326328 A1 | 12/2009 | Kucklick |
| 2010/0026940 A1 | 2/2010 | Takegami et al. |
| 2010/0121442 A1 | 5/2010 | Shea et al. |
| 2010/0203454 A1 | 8/2010 | Brongersma et al. |
| 2010/0268027 A1 | 10/2010 | Aono et al. |
| 2010/0286475 A1 | 11/2010 | Robertson |
| 2011/0124960 A1 | 5/2011 | St. Onge et al. |
| 2011/0152618 A1 | 6/2011 | Surti |
| 2012/0034573 A1 | 2/2012 | Erdmann et al. |
| 2012/0209074 A1 | 8/2012 | Titus |
| 2012/0209090 A1 | 8/2012 | Goodall et al. |
| 2012/0232342 A1 | 9/2012 | Reydel |
| 2013/0040516 A1 | 2/2013 | Pruneri et al. |
| 2013/0090527 A1 | 4/2013 | Axon |
| 2013/0144287 A1 | 6/2013 | Crowley et al. |
| 2013/0190562 A1 | 7/2013 | Smith et al. |
| 2013/0237998 A1 | 9/2013 | Wallace et al. |
| 2015/0073214 A1 | 3/2015 | Ueda |
| 2016/0051135 A1 | 2/2016 | Greenberg et al. |
| 2016/0270636 A1 | 9/2016 | Iwasaka et al. |
| 2017/0066111 A1 | 3/2017 | Wang |
| 2017/0311789 A1 | 11/2017 | Mulcahey et al. |
| 2018/0096191 A1 | 4/2018 | Siemens |
| 2019/0261912 A1 | 8/2019 | Shepherd et al. |
| 2019/0304093 A1 | 10/2019 | Duval et al. |
| 2019/0311476 A1 | 10/2019 | Hayami et al. |
| 2019/0384088 A1 | 12/2019 | Watanabe |

FOREIGN PATENT DOCUMENTS

| | | |
|---|---|---|
| EP | 1870018 A2 | 12/2007 |
| JP | H0373168 A | 3/1991 |
| JP | H09238893 A | 9/1997 |
| JP | 2000300570 A | 10/2000 |
| JP | 3124079 B2 | 1/2001 |
| JP | 2002233491 A | 8/2002 |
| JP | 2003033319 A | 2/2003 |
| JP | 2003339631 A | 12/2003 |
| JP | 2005066139 A | 3/2005 |
| JP | 2006026344 A | 2/2006 |
| JP | 2009261830 A | 11/2009 |
| WO | WO 9929362 A1 | 6/1999 |
| WO | WO 2001085319 A1 | 11/2001 |
| WO | WO 2006138409 A2 | 12/2006 |
| WO | WO 2007029230 A2 | 3/2007 |
| WO | WO 2007029814 A1 | 3/2007 |
| WO | WO 2007147060 A2 | 12/2007 |
| WO | WO 2009149042 A2 | 12/2009 |
| WO | WO 2011085319 A1 | 7/2011 |
| WO | WO 2011099329 A1 | 8/2011 |
| WO | WO 2011148172 A2 | 12/2011 |
| WO | WO 2014123563 A1 | 8/2014 |
| WO | WO 2017011535 A1 | 1/2017 |

OTHER PUBLICATIONS

Extended European Search Report for EP Appl. No. 16828548.4 dated Feb. 28, 2019.
Extended European Search Report for EP Appl. No. 16804476.6 dated Dec. 5, 2018.
Extended European Search Report and Written Opinion for EP Appl. No. 16804462-6 dated Dec. 10, 2018.
Extended European Search Report for EP Appl. No. 12747511.9 dated Jan. 3, 2018.
Extended European Search Report for EP Appl. No. 18174913.6 dated Aug. 16, 2019.
International Preliminary Report on Patentability issued in PCT/US2015/051662 dated Apr. 6, 2017.
International Search Report and Written Opinion for PCT Appl. No. PCT/US2019/012448 mailed Apr. 16, 2019.
International Search Report and Written Opinion dated Oct. 26, 2016 for PCT Application No. PCT/US2016/043371, filed Jul. 21, 2016.
International Search Report issued in corresponding International Application No. PCT/US2015/051662 dated Dec. 14, 2015.
International Search Report and Written Opinion dated Sep. 21, 2012 for PCT Appl. No. PCT/US2012/025404.
Japanese Patent Office, Notification of Reasons for Refusal, JP Appl. No. 2013-554596, Dec. 8, 2015.
Chinese Office Action and Search Report for CN Appl. No. 201280014363, Mar. 23, 2015.
Chinese Office Action for CN Appl. No. 201280014363, Jan. 5, 2016.
Chinese Office Action for CN Appl. No. 201680045602.6 dated Jun. 5, 2019.
First Examination Report for Indian Appl. No. 6566/CHENP/2013 dated Aug. 29, 2019.
Beneq Biocompatible Coatings Webpage.
Cargille Laboratories, Inc. Material Safety Data Sheet—Cargille Optical Gel Code 0607, Jun. 3, 2005.
Depth of Field, OPMI Application Tip #2, Informed for Medical Professionals in Neuro, ENT and Spine, 2nd Issue, Oct. 2006, Published by Carl Zeiss Surgical GmbH, Germany.
Jaxton, et al., An Experimental Investigation on the Development of Hydrogels for Optical Applications, Polymer Testing, 2003, 22(4):371-374, English Abstract.
Kopp, et al., Chapter 9, Optical Principles of the Endoscope, Hysteroscopy: Visual Perspectives of Uterine Anatomy, Physiology & Pathology, 3rd Edition, Lippincott Williams & Wilkins, 2007, 19 pages.
Maquet Training Manual, Vasoview 6 Endoscopic Vessel Harvesting System, Cardiovascular, Copyright Maquet Cardiovascular LLC, Oct. 2008.
Oil Immersion, From Wikipedia, http://en.wikipedia.org/wiki/Oil.sub.--immerson, Printed Sep. 7, 2010.
Olympus Colonoscopes Outpatient Doctor Surgery Center, http://outpatientsurgicare.com/index.PHP?Facilities:Technologies:Olympus.sub.--Colonoscopes&print, Printed Oct. 26, 2010.
Olympus Disposal Distal Attachment Product Data Sheet.
Olympus Evis Exera Colonovideoscope/Sigmoidovideoscope, Olympus CF Type Q1601JUS, Today's Most Versatile Choice for Colonoscopy, Product Data Sheet.
Olympus Technologies Evis Exera II, Learn About Wide-Angle, http://www.olympusamerica.com/msg.sub.--section/ msg.sub.--endoscopy.sub.---technology.asp, Copyright 2010 Olympus America Inc.
Olympus Technologies Evis Exera II, Learn About Close Focus, http://www.olympusamerica.com/msg.sub.--section/ msg.sub.--endoscopy.sub.---technology.asp, Copyright 2010 Olympus America Inc.
Olympus NA-11J-KB Product Data Sheet.
Optical Gels for Fiber-Optic Connectors and Splices—A Tutorial, Nye Optical Products, 6 pages.
Paxton, et al., An Experimental Investigation on the Development of Hydrogels for Optical Applications, Polymer Testing, 2003, 22(4):371-374, English Abstract.
Sigma-Aldrich Poly(2-hydroxyethyl methacrylate) Product Data Sheet, http://www.sigmaaldrich.com/catalog/Product Detail, Copyright 2010 Sigma-Aldrich Co.
Sigma-Aldrich Poly(ethylene glycol) Product Data Sheet, http://www.sigmaaldrich.com/catalog/Product Detail, Copyright 2010 Sigma-Aldrich Co.
Sigma-Aldrich Poly(vinyl alcohol) Product Data Sheet, http://www.sigmaaldrich.com/catalog/Product Detail, Copyright 2010 Sigma-Aldrich Co.

(56) References Cited

OTHER PUBLICATIONS

Sigma-Aldrich Methacrylic acid Product Data Sheet, http://www.sigmaaldrich.com/catalog/Product Detail, Printed Sep. 3, 2010.
SmartGel Nye Nyogel OCK-451LPH Product Data Sheet, Nye Optical Products.
Smeds, et al., Photocrosslinkable Polysaccharides for in situ Hydrogel Formation, Journal of Biomedical Materials Research, 2001, 54:115-121.
Stadler, Transparent conducting oxides—An up-to-date overview, Materials 5.4:661-683, 2012.
The Basics of Silicon Chemistry, Basic Silicon Production and Siloxane Polymerization, http://www.dowcorning.com/ content/sitech/sitechbasics/siloxane.sub.--poly- merization.asp, Copyright 2000-2010 Dow Corning Corporation.
Uw Eye Research Institute, Newsletter, Point of View, Summer 2009, http://vision.wisc.edu/news.sub.--sum09.html, Printed Feb. 5, 2010.
Vinyl Sustainability Forum 2014, Title: Benefits of PVC, Date retrieved: Mar. 7, 2014 from website: http://www.pvc.org/ en/p/benefits-of-pvc, pp. 1-4.
Zeng, et al., An Endoscope Utilizing Tunable-Focus Microlenses Actuated through Infrared Light, Solid-State Sensors, Actuators and Microsystems Conference, 2009, Transducers 2009, International, Issue 21-25, pp. 1214-1217, Abstract Only.
Zeng, et al., Tunable Liquid Microlens Actuated by Infrared Light-Responsive Hydrogel, Applied Physics Letters, 2008, 93:151101-1-151101-3.
Written Opinion of the International Searching Authority; issued in corresponding International Application No. PCT/US2021/025272, dated Aug. 24, 2021.

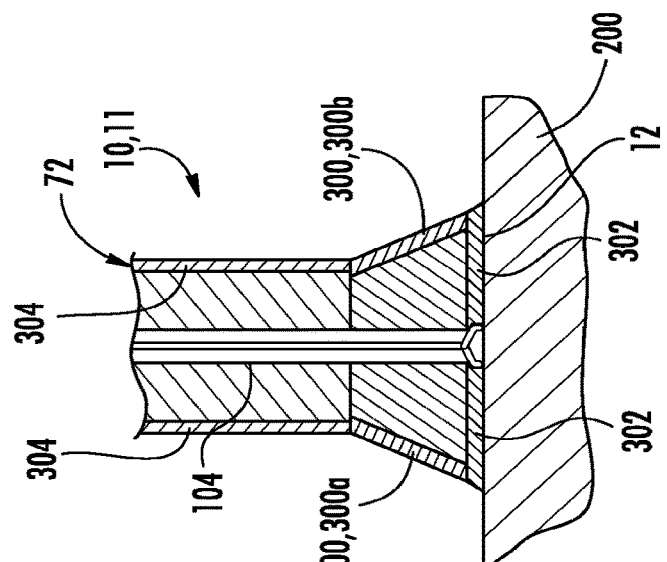
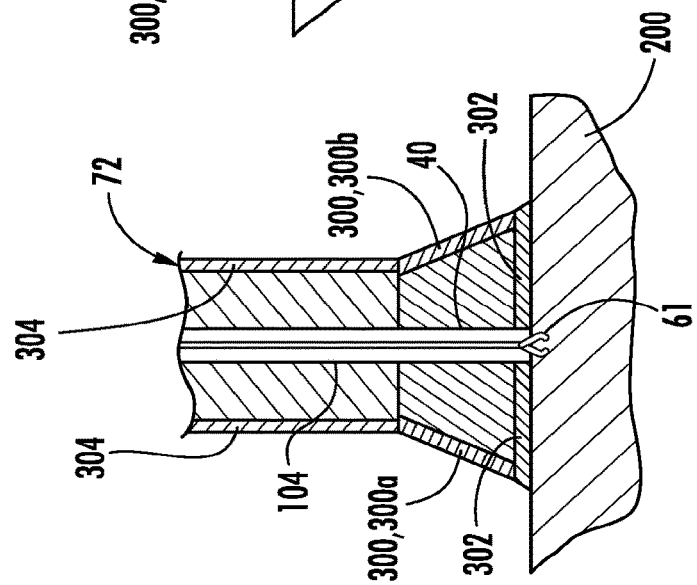
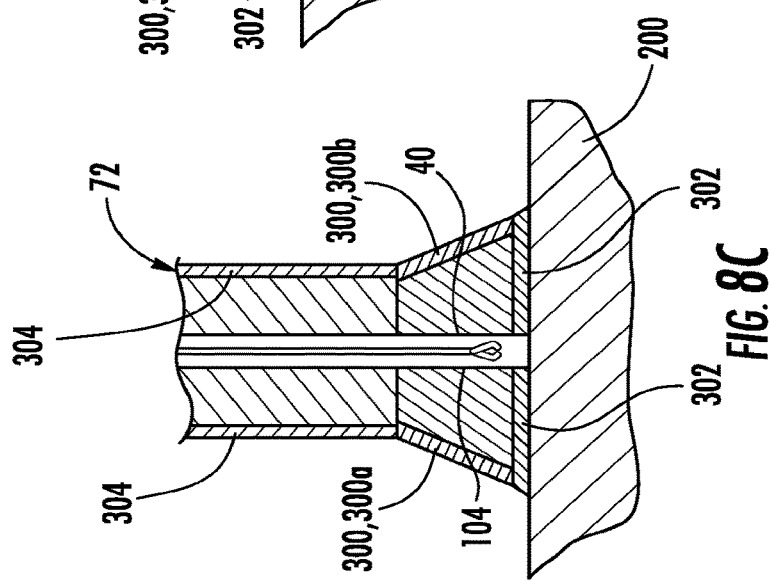
FIG. 8A
FIG. 8B
FIG. 8C

CONDUCTIVE OPTICAL ELEMENT

CROSS-REFERENCE TO RELATED APPLICATIONS

This application is a continuation of U.S. patent application Ser. No. 16/776,168, filed Jan. 29, 2020, which is a continuation of U.S. Pat. No. 10,548,467, filed Jun. 2, 2015, the entire disclosures of which are incorporated herein by reference in their entirety for all purposes.

BACKGROUND

Minimally and less invasive surgery, and interventional treatments, of patients are generally safer, faster, and less traumatic to the patient. These procedures therefore involves less inflammation, post-operative pain, infection risk, and reduced healing time compared to more invasive forms of surgery, including general and open surgery.

In medical applications, less invasive approaches usually involve either direct or remote visualization with hand or remote instruments used for diagnosis, treatment or manipulation. Applications include surgery using a small incision (called a mini-thoracotomy) and direct visualization of the surgical site. Alternatively, one or more forms of remote visualization may be used, such as an inspection of the colon using a flexible colonoscope or visualization of a surgical site using a laparoscope.

When engaged in remote visualization inside the patient's body, a variety of scopes are used. The scope used depends on the degree to which the physician needs to navigate into the body, the type of surgical instruments used in the procedure and the level of invasiveness that is appropriate for the type of procedure. For example, visualization inside the gastrointestinal tract may involve the use of endoscopy in the form of flexible gastroscopes and colonoscopes and specialty duodenum scopes with lengths that can run many feet and diameters that can exceed 1 centimeter. These scopes can be turned and articulated or steered by the physician as the scope is navigated through the patient. Many of these scopes include one or more working channels for passing and supporting instruments, fluid channels and washing channels for irrigating the tissue and washing the scope, insufflation channels for insufflating to improve navigation and visualization and one or more light guides for illuminating the field of view of the scope.

Smaller and less flexible or rigid scopes, or scopes with a combination of flexibility and rigidity, are also used in medical applications. For example, a smaller, narrower and much shorter scope is used when inspecting a joint and performing arthroscopic surgery, such as surgery on the shoulder or knee. When a surgeon is repairing a meniscal tear in the knee using arthroscopic surgery, a shorter, more rigid scope is usually inserted through a small incision on one side of the knee to visualize the injury, while instruments are passed through incisions on the opposite side of the knee. The instruments can irrigate the scope inside the knee to maintain visualization and to manipulate the tissue to complete the repair.

Other scopes may be used for diagnosis and treatment using less invasive endoscopic procedures, including, by way of example, but not limitation, the use of scopes to inspect and treat conditions in the lung (bronchoscopes), mouth (enteroscope), urethra (cystoscope), abdomen and peritoneal cavity (laparoscope), nose and sinus (laryngoscope), anus (sigmoidoscope), chest and thoracic cavity (thoracoscope), and the heart (cardioscope). In addition, robotic medical devices rely on scopes for remote visualization of the areas the robotic device is assessing and treating.

These and other scopes may be inserted through natural orifices (such as the mouth, sinus, ear, urethra, anus and vagina) and through incisions and port-based openings in the patient's skin, cavity, skull, joint, or other medically indicated points of entry. Examples of the diagnostic use of endoscopy with visualization using these medical scopes includes investigating the symptoms of disease, such as maladies of the digestive system (for example, nausea, vomiting, abdominal pain, gastrointestinal bleeding), or confirming a diagnosis, (for example by performing a biopsy for anemia, bleeding, inflammation, and cancer) or surgical treatment of the disease (such as removal of a ruptured appendix or cautery of an endogastric bleed).

Direct and remote visualization devices, such as scopes used in endoscopy, robotic and other medical procedures, transmit images to the viewer in a variety of ways, through the use of image capture elements, including (i) relay lenses between the objective lens at the distal end of the scope and an eyepiece, (ii) fiber optics, (iii) charge coupled devices (CCD) and complementary metal oxide semiconductor (CMOS) sensors, as well other image capture and transmission methods known to one reasonably skilled in the art. A typical endoscope consists of an element which holds an image capture element and (often) a light source that illuminates the field of view of the scope (such as light directed by an LED or fiber system). Frequently, a video capture system is connected to the visualization device to display a video image on a display monitor that can be viewed by a user during use of the visualization device. The system may include an ability to adjust the focus of the display through manual adjustments or an autofocus capability in a video processor system used with the optical imaging device.

Additional devices are used with remote visualization devices to effect treatment or repair in medical and non-medical procedures. For example, with medical applications, it is common to use a separate device, such as a grasper, to manipulate and shift tissue to obtain a different vantage point and to use a third device to cauterize or ablate tissue if there is bleeding or disease that can be treated effectively with this approach. These devices are often used through a different point of access, such as a separate incision or a port, or are used through working channels designed into certain scopes, such as colonoscopes.

There exists a need to improve the overall visualization and manipulation of tissue and other matter through the addition of more therapeutic and repair capabilities for use with scopes and other optical elements.

SUMMARY

Implementations of the present disclosure overcome the problems of the prior art by providing a device including an optical element, one or more conductive coatings and at least one connector area to deliver energy to the device. The conductive layer coating may be at least partially optically transparent. It may include a conductive oxide, such as a titanium oxide or an aluminum oxide, or other conductive materials.

The connector area may be configured for connection to a power source. The connection to the power source may be part of the device. Also, the device may connect to a catheter (such as by a flex transistor or wire), cord or other element which connects to the connector and the power source. The power source may be part of the device. Power sources may include an electrical energy generator, an electrosurgical generator, a coblation generator, an argon gas generator, an ultrasound generator, a plasma generator or any other form of generator or other power source (including a battery) which can make and transmit energy to or across an optical element or a conductive coating.

The device may be removably placed on a remote visualization device. The device may also be designed as a permanent element of a remote visualization device, such as a scope.

The optical imaging element may be configured to shed fluid, debris and particulate matter, to remain distant from tissue or other matter, or to contact tissue or other matter, and to manipulate and shift the tissue or other matter, including manipulation, reorientation conforming the tissue to a desired shape or dissection. The conductive coating may be configured to generate sufficient energy to alter the tissue or other matter. The conductive coating or coatings may be applied to the device to create a single electrode to alter the tissue or other matter. The conductive coatings may also be applied in multiple patterns on the device, to create multiple electrodes to alter tissue or other matter in more than one way. Tissue or matter alteration may, for example, include ablation, coblation, cauterizing, shaping, sealing, dissecting, debriding, resecting, cutting and coagulating tissue, evaporating blood or fluid, activating and curing glues and other chemicals or formulations activated by energy and other results associated with the delivery of energy to manipulate or alter matter.

An area of the conductive coating may be at least partially optically transparent. The optically transparent areas may be overlapping and positionable on tissue and other matter being manipulated and energized. The conductive coating may have a thickness of half a micron or less or such other thickness to create a specific tissue or matter alteration with the given power source and the intended application. The conductive coating may be uninsulated, or may be partially insulated or fully insulated through another material, including one or more dielectric coatings or materials.

The conductive coating may be configured to convert a power source to one or more forms of energy for the alteration of tissue or other matter, including monopolar energy, bipolar energy, argon gas energy, coblation energy, plasma energy, thermal energy, ultrasound, focused ultrasound or other forms of energy which can be transmitted across or through a conductive coating to alter tissue or matter. One or more biocompatible materials and any other materials reasonably suitable may be selected or configured to facilitate adherence of the conductive coating and the overall performance of the device.

The optical coupler and/or its connector and power source may have one or more feedback elements for determining the degree of alteration of tissue or matter.

These feedback elements may include one or more temperature sensor(s), thermocouple(s), or other elements for the measurement of the alteration, impact or effect of one or more forms of energy when applied to tissue or other matter.

In another implementation, a method includes contacting at least a portion of the tissue or matter with an optical element; applying energy to a coating on the optical element and altering the portion of the tissue or matter. The tissue or matter is altered by conducting energy onto or through the portion of the tissue or matter using the coating on the optical element as an electrode to deliver energy.

Altering the tissue or other matter may include heating, cauterizing, shaping, sealing, dissecting, resecting, debriding, cutting, coapting, coagulating, coblating, ablating or other manipulation involving contact of the tissue or matter with the energy delivered through or across the coating. Applying energy may include applying a bipolar electrical energy through or across a surface of the optical element. Contacting the tissue or matter may include coapting the tissue or matter, coagulating, sealing a vessel of the tissue or other manipulation involving contact of the tissue or matter with the energy delivered by the coating on the optical element.

One or more of the coatings used on the optical element may have different water contact angles to facilitate different performance elements with the optical element, including coatings with water contact angles creating hydrophilic performance, hydrophobic performance and super hydrophobic performance. One or more of the coatings may also have anti-reflective properties to reduce or minimize reflection of light in the field of view of the scope and other variants of the coatings may have anti-scratch and other hardness properties to protect the optical element. The coatings may also be conductive and may be transparent.

Embodiments of the optical element may include the ability to irrigate the tissue or matter and the ability to inject one or more drugs, glues or other compounds into a targeted area for energizing and manipulation by the device. In another aspect, the scope is a means for viewing within the body.

One embodiment includes a device comprising: an optical element; a conductive material disposed on at least a portion of the optical element; and at least one connector capable of providing energy to the conductive material. In another aspect, the optical element is integrally mounted on a distal end of a scope. The optical element may be a lens with the portion being an outer, distal surface of the lens. And, the scope may be a means for viewing within the body.

In another aspect, the connector is configured for connection to a power source. The conductive material may be at least partially transparent. And, the device may additionally include a power source. For example, the power source may be selected from the group consisting of: an electrical energy generator, an electrosurgical generator, a coblation generator, an argon gas generator, an ultrasound generator, cyrogenerator and a plasma generator.

Another embodiment includes an assembly comprising: an image capture device having a viewing end; a positioning assembly supporting the viewing end; a conductive surface on the viewing end, the conductive surface positioned and configured to conduct energy over the viewing end; and a power source connection configured to supply the energy to the conductive surface. The positioning assembly may include an elongate member configured for insertion through restricted openings. The positioning assembly may also include controls coupled to an end of the elongate member opposite the viewing end.

The image capture device may be configured to transmit fluid to the viewing end. The image capture device may, for example, include a working channel. And the working channel may be configured to transmit fluid.

In another aspect, the conductive surface may be optically transparent. And, the conductive surface may be able to overlap or conform to the tissue.

The conductive surface may be connected to the power source by a second conductive surface, such as a platinum surface.

Advantages of the implementations include (i) improved visualization in fluid, debris and blood, (ii) the ability to turn the scope into a therapeutic device by delivering energy to a target area through the optical element on the scope, eliminating the need to engage in a separate instrument exchange to delivery energy to tissue or other matter, (iii) the ability to provide lens anti-fogging capability, (iv) the ability to control energy delivery to treat narrow to broader areas of matter and tissue without missing a targeted area because of the ability to maintain visualization throughout the application of energy, (v) the ability to use the working channel in certain variants of the device to deliver a complementary device such as a grasper while maintaining the ability to delivery energy at any time concurrently, and (vi) other benefits including improvement of procedures in medical applications such as in diathermy, electrocauterization, electrosurgery, biopsy, ablation, coblation, fogging reduction, as well as improvements in non-medical applications such as pipeline inspections and repairs using remote visualization. These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

FIG. 1;

FIGS. 8A, 8B and 8C show a cross-sectional view of a device of another implementation of the present invention;

DETAILED DESCRIPTION

Figure 1:
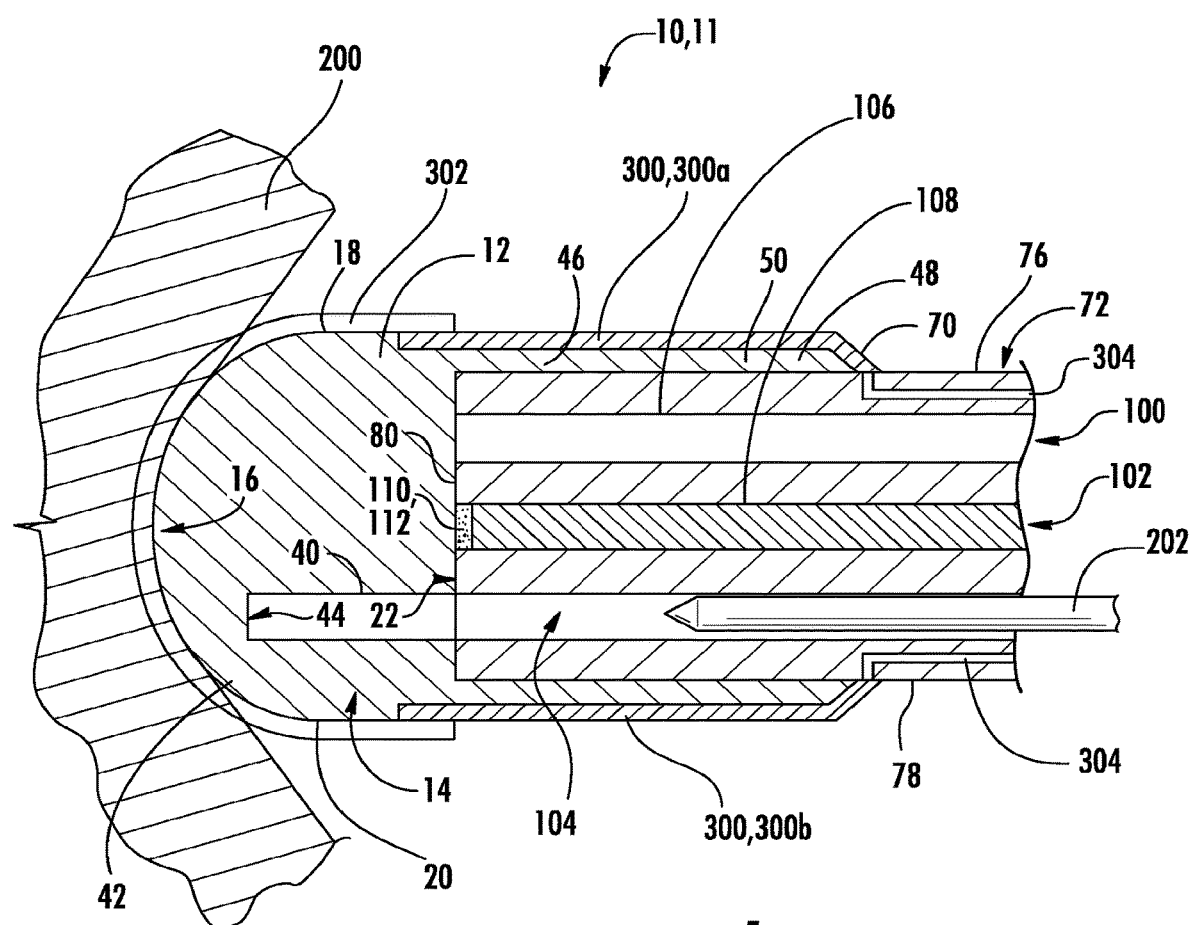
FIG. 1 shows a cross-sectional side-elevation view of a device of one implementation of the present invention including an optical coupler attached to the distal end of an endoscope.
Figure 3:
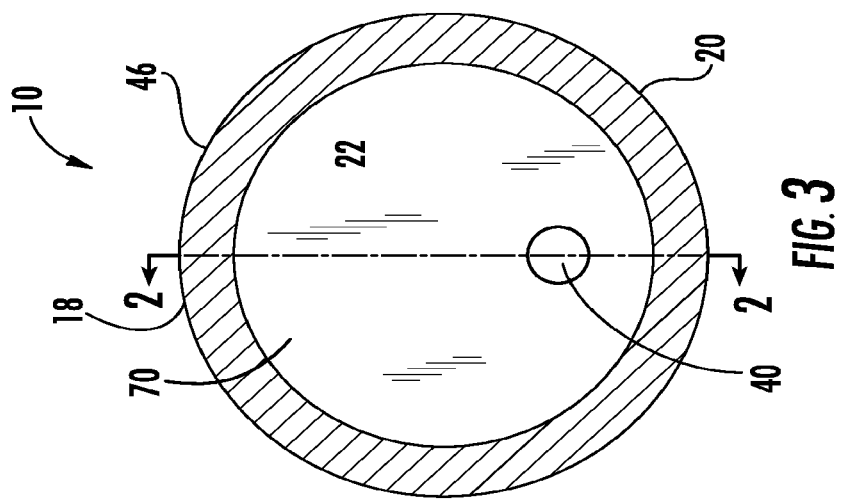
Figure 2:
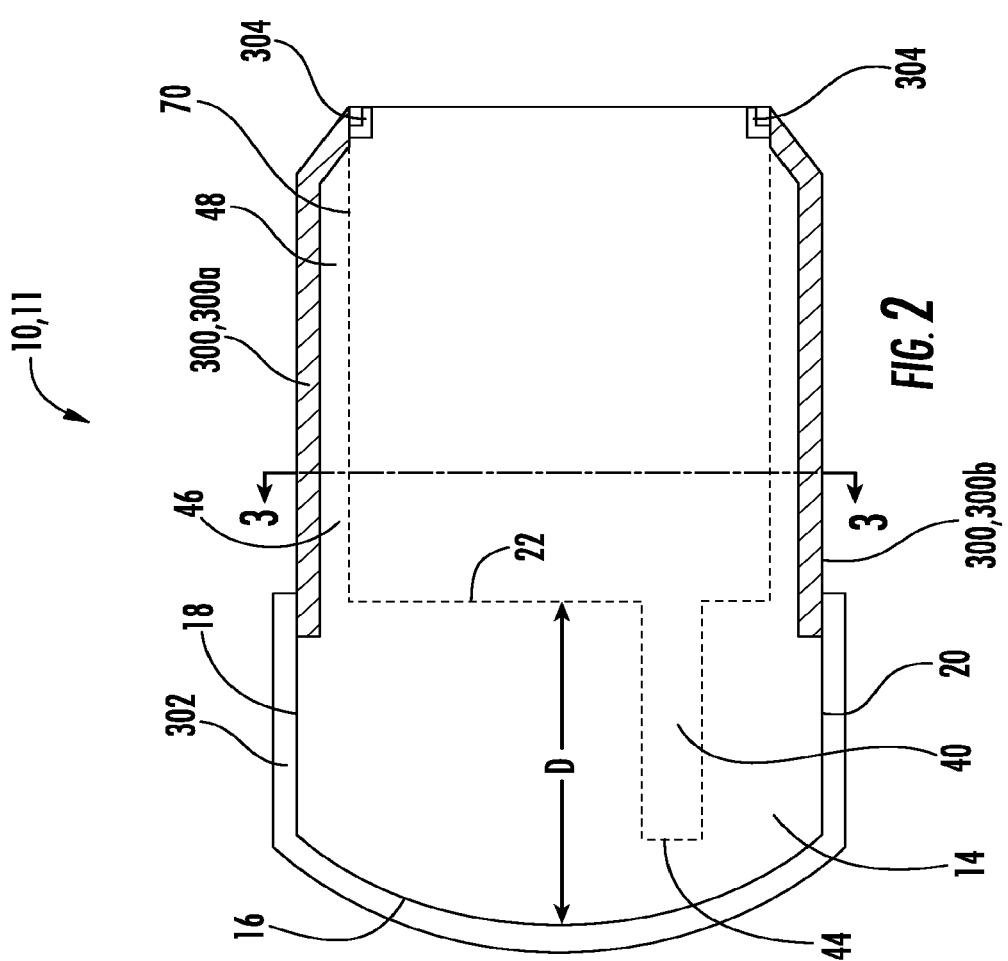
FIG. 2 shows a cross-sectional side-elevation view of the optical coupler of FIG. 3 shows a rear, sectional elevation view of the optical coupler of FIG. 1.

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

The inventors have observed that despite the many benefits associated with using image capture devices to improve visualization, including remote visualization, to diagnose and treat patients in a medical context or, separately, to inspect and fix conditions in nonmedical applications, there still are significant issues with these technologies where improvement is needed. Image capture elements quickly become clouded with fluid, debris and particulate matter which obscures visualization. In addition, image capture elements may be dependent on instruments and other elements to provide therapy and to modify, manipulate and repair matter.

In non-medical applications, less invasive inspection and repair of remote areas and defects in non-medical settings, whether involving a sewer trunk line, a hydraulic line, an oil pipeline, a gas line or other non-medical areas in which inspection and/or repair can be obtained with less disruption and intrusion, is generally superior to opening up the area more invasively to inspect and repair.

In non-medical applications, direct visualization may be achieved through the use of small ports. For example, by drilling a hole into a pipeline to inspect the line at a specific point. Another example is the use of a borescope to remotely navigate and advance through the pipeline to visualize the area of inspection for possible remote repair.

With non-medical applications, such as oil pipeline inspection, robotic arms with grasping and articulation capability are used with the remote visualization device to diagnose and repair.

Remote visualization devices and associated elements are also common to non-medical scopes used for remote visualization including rigid and non-rigid borescopes, videoscopes, flexoscopes, fiberscopes and other scopes used for remote visualization in non-medical applications.

Generally, the inventors have found that these instruments need to be advanced, retracted and exchanged through incisions, ports, working channels or other points of access. This approach means the correct instrument is not always readily available when needed. For example, when performing a laparoscopic surgery case, a blood vessel may be cut and a bleed occur, while the physician is engaged in fine dissection of tissue to access a treatment point. The physician may not have a cautery or vessel sealing instrument in one of the ports used to advance and retract instruments in the patient for treatment. When this occurs, the bleed will continue while the physician retracts one of the instruments and inserts a cautery device or a vessel sealing device (called a device exchange) to try and then find the bleed and stop it. Due to the time it takes to complete the device exchange, the bleeding area may become filled with blood, obscuring the location of the bleed. Further, during this time, the scope may become covered with blood, debris or other fluid, or may fog causing additional issues that complicate finding and treating the bleed.

Similar limitations arise with scopes that have working channels. For example, when performing a colonoscopy and excising a pre-cancerous polyp to diagnose whether cancer is present, a vessel may inadvertently be cut, causing a lower gastrointestinal bleed. To treat the bleed, the physician must perform an exchange of instruments, withdrawing the device out of the working channel of this long, flexible scope (200 centimeters long) and inserting and advancing a cautery device down the working channel of the scope. The location of the scope and the bleed must then be confirmed (as the scope may shift) and then cautery is attempted to address the bleed. This effort may be hindered by fluid, debris and blood which obscures the scope's visualization. In addition, the application of cautery is very limited. This is because the cautery device can be restricted to no wider than the diameter of the working channel in the scope, which is typically between two and three millimeters. Hence, the cautery lesion from current devices is usually only a few millimeters wide, necessitating multiple cautery attempts to treat longer or wider or uneven bleeding areas with current technology.

This same set of issues and other issues apply with other scope applications, including the treatment of upper gastrointestinal bleeds. Further, other issues and limitations apply with scopes that do not have a working channel, but must be advanced some distance from the user. For example, such issues occur in borescopes in non-medical applications and certain ear, nose and throat medical applications. These issues also apply to other applications that depend on a scope for visualization, including robotic navigation and robotic surgery and treatment.

Implementations of the present disclosure overcome the problems by providing a device having an optical element with a conductive coating. The device 11 of one implementation, for example, as shown in FIG. 1, comprises an optical element 10, a conductive material 302 and at least one connector 300. The conductive material 302 is disposed on at least a portion of the optical element 10. The optical element, for example, may be an object lens of an endoscope 110 or an optical coupler. The connectors (acting as terminal(s)) 300, 300a, 300b are capable of providing energy (such as electrical energy) to the conductive material 302. In one aspect, the conductive material is an optically transparent material.

Advantageously, the device 11 allows visualization of an object—such as body tissue or other matter 200—concurrent with the application of energy to the object via the conductive coating. This allows the user to observe the alteration of tissue and other matter in real time as the energy is delivered. For example, the device 11 can provide electrical energy via the transparent conductive material 302 to cauterize the tissue 200 at the same time the tissue is being directly viewed through the endoscope 72 and the optical element on the endoscope.

As shown in FIG. 1-4, in embodiments, the optical element 10 may be a type of optical coupler that includes a visualization section 12 at a distal end 14 and an attachment section 46 at a proximal end 48. The optical coupler 10 is configured for attachment, via the attachment section 46, to a remote visualization device, such as an endoscope 72. In embodiments, the optical coupler 10 is comprised of a transparent material, at least a portion of which may cover the optical area of the underlying endoscope 72 to keep it clear of obscuring debris in the body. Also, the outer surfaces of the optical coupler 10 can displace fluid, blood, debris and particulate matter on tissues being inspected by the endoscope 72. Additional details of such optical couplers are disclosed in U.S. Patent Application Publication No. 2013/0110097 filed Sep. 17, 2012, which is hereby incorporated herein by reference.

Referring again to FIG. 1, the visualization section 12 includes a distal, outer surface 16 spaced apart from a proximal surface 22. In embodiments, at least a portion of the visualization section 12 covers some or all of the optical area of the endoscope 72. The outer surface 16, in FIG. 1, has a rounded, convex shape. The outer surface 16, for example, curves continuously from a first outer side boundary 18 across to a second opposite outer side boundary 20 of the visualization section 12. In embodiments, the outer surface may also be convex but off-centered, concave, flat, or positioned at an angle, to the optical lens of the endoscope. For example, the outer surface may be positioned at an angle slopping away from or, alternatively, sloping to the optical lens of the endoscope. A healthcare worker may advance the outer surface 16 into contact with the tissue or other matter 200 and still maintain visualization because of the design of the optical coupler. In addition, the healthcare worker, by making contact with the tissue or other matter with the optical coupler on the scope, is able to displace fluid, blood, debris and particulate matter from the field of view. This provides a better view of the underlying tissue or matter for assessment and therapy, including the delivery of energy through this device. The shape of the outer surface 16 may be a-traumatic.

Also, in other embodiments, the device may have one or more channels to enable the passing of instruments through the scope and the device or to provide irrigation or insufflation, or to expose the light guides of the scope to alter the performance of light in certain environments. For example, these channels may be hollow and pass through the outer surface of the device. The channels may also be self-sealing and therefore not pass all the way through the outer surface of the device to seal the channel when the channel is not in use. In other embodiments, more than one channel may be present. One channel may align with the working channel of the scope and the device, allowing for the passing of instruments. Another channel may allow fluid and air to emit from the scope and pass through the device. A third channel may redirect fluid from the fluid water on the scope to the working channel in the device and out beyond the outer surface of the device.

The visualization section 12 can be formed from a range of materials that provide improved visualization of objects for the endoscope 72. For example, the visualization section may be formed of a transparent material capable of transmitting an optical image of the surface area. While any type of (at least partially) transparent material may be used, materials that adhere well (and stay adhered) to the conductive material 302 are particularly desirable. Particularly well-suited are materials that have an attractive index of refraction and level of light transmission. Also desirable is a stability when used with energy applications to minimize the impact of the substrate on the conductive materials and the impact of the energy delivery on the optical performance. For example, polycarbonate materials are a well-suited material for the visualization section because of polycarbonate's index of refraction and performance across various temperature ranges. Additional materials include acrylic, polystyrene, cyclic olefin copolymer, polyetherimide, glass, silicone and other optical materials. These materials provide a combination of a relatively low index of refraction, high light transmission and appropriate temperature performance, including insulation properties and relatively low levels of thermal expansion when used with the application of various forms of energy.

In other embodiments, a device using more than one material may connect the materials through glue or other chemical bond, molding the materials together, over-molding one material on the other material, placing a mechanical connector between the materials, or over the materials, or a combination thereof. Connections may also be made by coating one material onto another, screwing one material on to the other, or other ways of connecting one material to another wherein at least one of the materials is a substrate for a conductive coating.

The term "transparent" as used herein is not always limited to optically transparent. Instead transparent may include the ability to or characteristic of passage of energy waves, including infrared and/or ultraviolet rays. Transparent also need not be limited to perfectly transparent and instead could refer to some ability to facilitate or allow passage of light rays (e.g., translucent).

Alternatively, the coupler 10 may not be formed of a transparent material and in embodiments can be made from one or more materials suitable for the particular remote visualization application. In embodiments, for certain applications, the coupler may serve as a support and applicator for the conductive material 302 with either limited or no ability to improve visualization.

Figure 4:
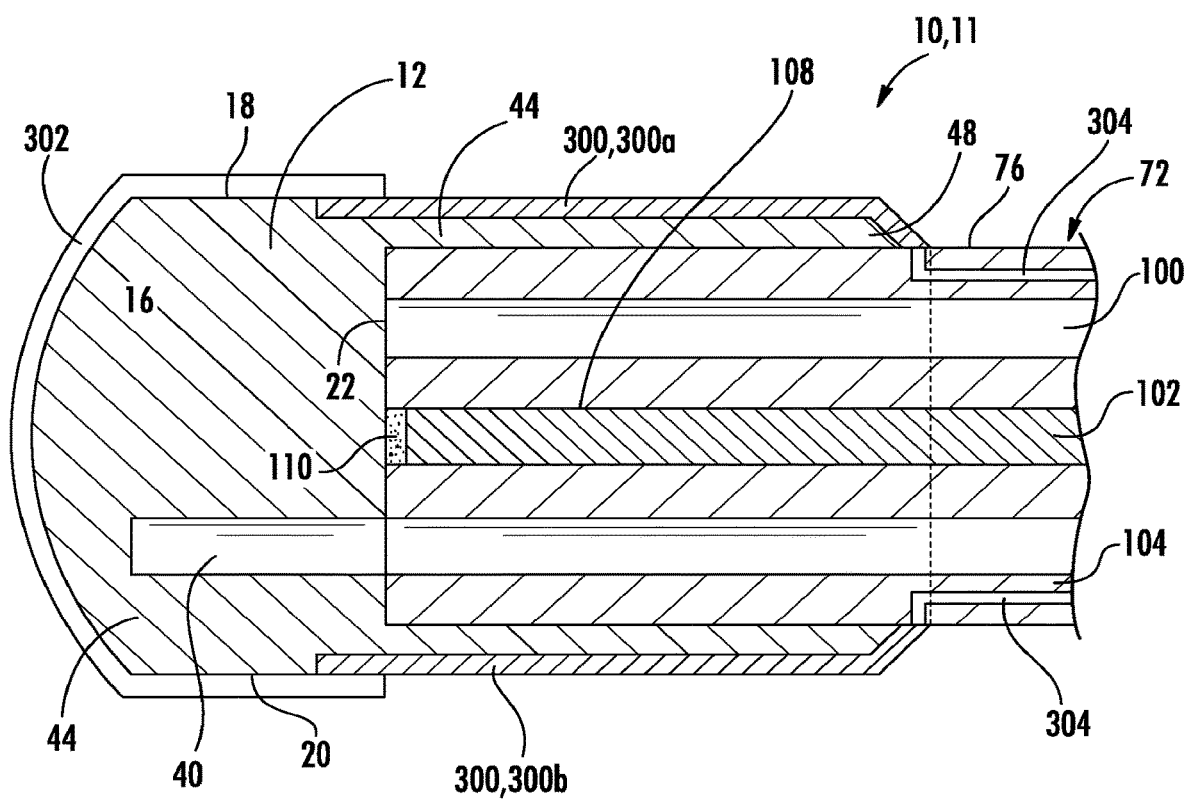
FIG. 4 shows another cross-sectional view of the device of FIG. 1.

As shown in FIG. 4, the attachment section 46 may include a cylindrical wall 50 extending from the proximal end 48 of the optical element 10. Generally, the attachment section 46 is configured to mate with and secure the visualization section 12 to the end of the endoscope 72 or other optical imaging device. To this end, the cylindrical wall 50 is sized to define a hollow cylindrical opening 70 for a press or other secure fit onto the distal end of the endoscope 72. It should be noted that the attachment section 46 may also include other structure to facilitate attachment and/or may be secured by welding, adhesive, screwing, mechanical connectors, interference between one or more materials and the optical imaging device, or such other form of connection between the device and the remote/optical imaging device. Also, the attachment section 46 need not have a cylindrical shape but instead can be formed to match the distal end shapes of various optical imaging devices or remote visualization devices. Or, the attachment section may be shaped to facilitate other functions of the device, including shaping the sides and distal end to conform to and manipulate tissue and matter more effectively. Shapes and materials may be selected to make the device less traumatic when contacting tissue and other matter. The visualization section of the device could also be integrated into a remote visualization device.

As shown in FIGS. 1 and 4, the endoscope 72 includes a sheath 76 having a distal end and supporting an optical assembly. The sheath 76 is a generally elongate member configured to enter and extend through passageways to provide remote visualization in the body and other passages. In some embodiments, endoscopes include some form of positioning assembly (e.g., hand controls) attached to a proximal end of the sheath 76 to allow the operator to steer the scope. In other embodiments, the scope is part of a robotic element that provides for steerability and positioning of the scope relative to the desired point to investigate and focus the scope. The sheath 76 also includes a distal end 74, as shown in FIGS. 1 and 4, extending into the cylindrical opening 70 of the optical coupler 10.

The sheath 76 may include one or more openings or lumens extending there-through for various purposes. For example, as shown in FIGS. 1-4, the sheath 76 defines a first lumen 100, a second lumen 102 and a third lumen 104. Each lumen extends from the proximal end to the distal end 74 of the sheath 76. The first lumen 100 may, for example, provide a passageway where a light guide 106 can be positioned in for transmitting light toward distal end 74. The second lumen 102 may provide a passageway to contain a remote visualization lens, camera, sensor, fiber or other element 108 for carrying the visual information back up to the proximal end of the sheath 76. The third lumen 104 may provide a passageway through which additional instruments, such as a wire, a catheter, biopsy forceps, guide wire, or other instrument 202, can be extended to the tissue or other matter 200.

As mentioned above, the sheath 76 in the embodiments of FIGS. 1-4 provides access for the optical assembly. In some embodiments, the optical assembly includes the light guide 106, and the image capture element 108, and object lens 110. As also mentioned above, the light guide 106 may transmit light from the proximal end of the sheath 76 to the distal end to illuminate the body tissue 200. The object lens 110 is positioned at the distal end of the optical fiber 108 and is configured to direct and focus the reflected light back to the distal end of the optical fiber. Generally, the object lens 110 can be any optical device that can transmit and refract light, including compound lenses which include an array of lenses with a common axis.

As shown in FIG. 1, upon securing the attachment section 46, the cylindrical wall 50 extends over an outer surface 78 of the distal end 74 of the sheath 76. And, the proximal surface 22 abuts an end surface 80 on the distal end of the sheath 76. Also, the third lumen 104 is aligned with a hollow instrument receptacle 40 defined in the visualization section 12 of the optical coupler 10.

As shown in FIG. 1-4, the conductive material 302 may be applied in a variety of configurations to create one or more electrode designs, depending on the desired effect with tissue and other matter. The electrode designs may be varied to suit the needs of other applications, such as inhibiting fogging of the remote visualization element or creating a combination of capabilities, such as a visualization element that can be warmed intermittently or continuously to inhibit or prevent fogging. An electrode design may also address the ability of the conductive material 302 to rapidly increase the energy delivery when needed to contact and cauterize or ablate tissue or other matter.

Heating an optical lens component with a conductive coating allows for continuous heating to prevent a significant temperature differential at the end of the scope or optical element. (The distal end is where the camera is often located and where the fogging can be a problem.) The temperature difference can create fogging, obscuring visualization through the scope or optical element. In addition the materials of the optical coupler (for example, such as silicone and polycarbonate) have insulation properties that facilitate antifogging. Anti-fogging can be accomplished for example by heating the optical element to about body temperature. Without being bound by theory, the inventors believe that the temperature difference at the distal end of the scope can range from about 95 degrees to 110 or even 120 degrees Fahrenheit, particularly if certain heat generating instruments are used, such as a harmonic scalpel, which raises the temperature around the end of the scope. Generally, then antifogging applications are lower power and temperature than cautery or other tissue modification temperatures.

In some embodiments, the conductive material may be in the form of a layer, strip, particle, nanoparticle or other shape applied in some discrete, continuous or intermittent pattern and in various combinations thereof. Variations in the shapes or patterns of application of the conductive material are possible within the capabilities of adding one material to another by adhering or combining the coating and other materials to achieve a desired result.

The conductive material can comprise a transparent conductive oxide (TCO), a conductive metal such as platinum, a polymer, or an organic semiconductor or such other materials able to conduct or transmit energy across the device. The term "layer" refers to at least some area of the conductive material 302 having a relatively uniform thickness and/or the method of application of the conductive material 302. For instance, the conductive material may be formed or applied through dipping, deposition coating, spraying, sputtering, ultrasonic application, brushing, painting, or such other application of the conductive material able to form a layer or other pattern on the intended substrate. In some embodiments, the conductive material may be of a uniform material thickness. In other embodiments, the conductive material may have a varying thickness. No part of the conductive material 302 need be of an exact thickness—it could vary continuously throughout. Instead, material thickness can be varied depending on the intended electrode function, such as the target level of resistance (and its variations) across the coating for the specific application.

Further, the conductive material 302 may be applied to form particular shapes (other than a layer) meant to apply energy in different patterns and densities to matter. Also, the conductive material 302 may be applied in a non-layer like manner, such as by being formed in a mould and then adhered, welded or otherwise attached to the optical element. Again, the shape of the conductive material 302 instead may correspond to the desired pattern of energy application by the conductive material, including a specific electrode design involving the conductive material and connectors to the conductive material 300.

In embodiments, the conductive material layer is applied to the distal end 14 of the optical element so that it extends over a portion of the visualization section 12. In one implementation, the portion of the visualization section 12 covered by the conductive material includes the entirety of the distal, outer surface area 16 of one side of the visualization section. However, the portion of the visualization section may include only a portion of the surface area of one side of the visualization section or may include one or more gaps between multiple applications of the conductive material layer, depending on the desired electrode design and desired result. For example, the conductive material 302 may only cover an area within the field of view of the objective lens 110 of the endoscope 72 or may be applied in part of the field of view or even be outside of the field of view. In other alternatives, the conductive material 302 may be applied in a pattern (strips, stripes, dimples, voids, undulations, curves, circles, semicircles), irregular, and such other approaches to create an electrode for an intended result applying energy with the device 200.

As shown in FIG. 1-4, the device 11 may also include one or more connectors 300 to provide energy to the conductive material. The connectors, in this implementation, include a first positive terminal 300a and a second negative terminal 300b. Electrical current flows from the positive terminal, through the conductive material 302 (energizing the conductive material) and out through the negative terminal.

The terminals can themselves be comprised of inert electrodes such as graphite (carbon), platinum, gold, and rhodium. Additionally the terminal may comprise copper, zinc, lead, and silver, or aluminum, or the conductive material or any other material known to one skilled in the art to be appropriate for transmitting energy. The wires 304 or other means of power transmission connect the electrode to a power cable (not shown) and may be embedded within the sheath 76 of the endoscope 72 and run parallel and close to the hollow instrument receptacle 40.

Alternatively, the wires or other means of power transmission may pass through (not shown) the visualization section in the instrument receptacle 40. The wires may also be delivered in another alternative manner, including inductive transmission of current to the device or to a battery embedded in the device. Power may also be supplied by current from a battery, a catheter, a cable, radio waves or other power transmission devices or methods capable of extending a distance to a terminal or connector.

Figure 13:
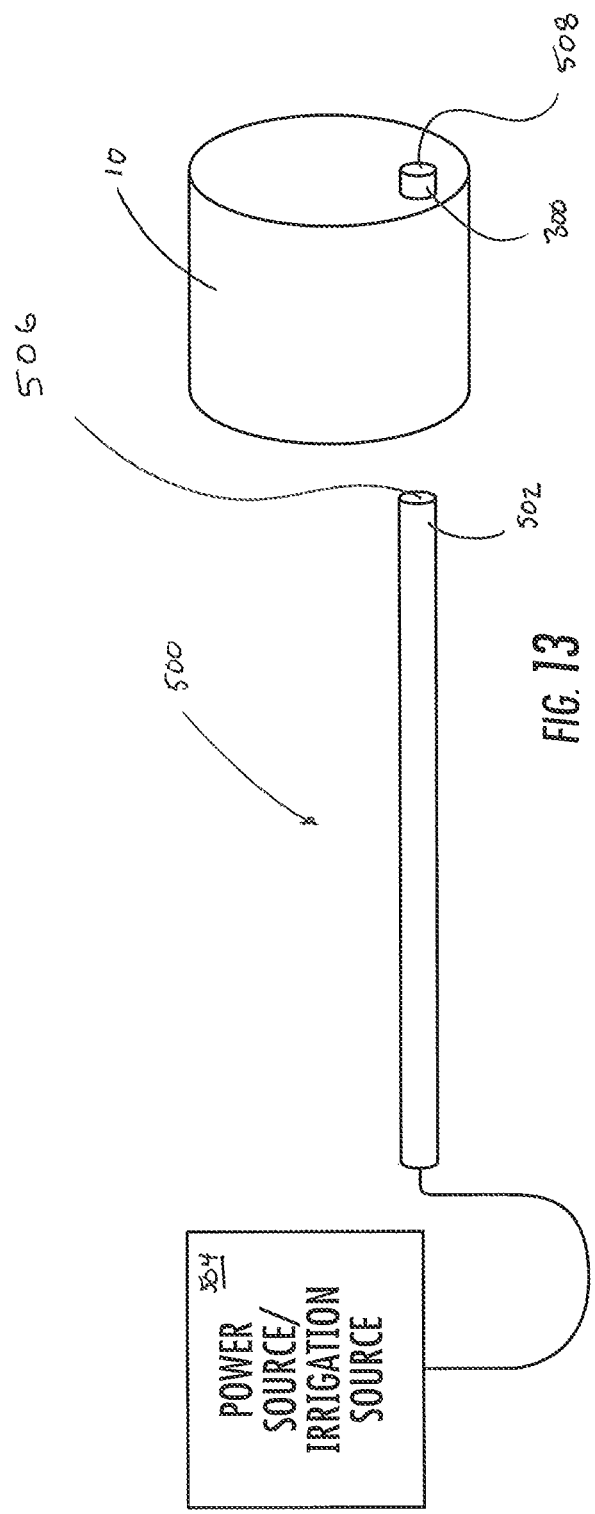
FIG. 13 shows another implementation of the present invention with a catheter providing energy from a power source to a connector in the device.

FIG. 13, for example, shows an energy catheter 500 configured to extend through a channel of a delivery catheter. The energy catheter includes a connector 502 at its distal end. An elongate body of the energy catheter 500 defines an irrigation channel 506. The energy catheter connects to a power and/or irrigation source 504 at its proximal end. The energy catheter 500 is configured for extension through the scope and into the working channel 508 of the optical coupler 10. Extension continues until the connector 502 abuts and/or otherwise mates or connects with corresponding contacts or terminals 300 communicating with the working channel.

The terminal or terminals 300 may be any device (including radio waves, induction or other wireless connection) that delivers energy of some kind to the conductive material 302. The conductive material itself, in the case of wireless excitation or extension of the conductive material into a shape for mating or communicating with an energy generator (or other power source) for example, may form or include the terminals 300.

It should be noted that the optical element 10 (in the form of a coupler, lens, coupler or other attachment, or integrated as part of the scope) can be used with a range of different scopes or other image capture devices. The term coupler here refers more generally to an optical element attached over the scope or integrated as part of the scope—which may include one integrally formed or attached to the scope or other technology for capturing and transmitting an image. The term "coupler" as used herein refers to a separately manufactured and/or separately, later attachable coupler, cap or lens.

The optical element can be adapted for use with optical capture elements of various sizes, including, relatively large telescopes, for example. Or, the optical element 10 can be the objective lens of the telescope wherein the device 11 is formed by disposing the conductive material 302 on at least a portion of the lens of the telescope and providing at least one terminal 300 for providing energy to the conductive material 302 on the lens. This may be useful for example, to prevent fogging on the lens. The optical element could also be used with, or be a portion of, a microscope in the same fashion. Other scopes that can be used with or for the optical element include: hydroscopes, haploscopes, culpascopes, ecoscopes, fiberscopes, videoscope, stauroscopes, stereoscope, and rhinoscope.

Also, the term "endoscope" refers generally to any scope used on or in a medical application, which includes a body (human or otherwise) and includes, for example, a laproscope, arthroscope, colonoscope, bronchoscopes, enteroscope, cystoscope, laparoscope, laryngoscope, sigmoidoscope, thoracoscope, cardioscope, and saphenous vein harvester with a scope, whether robotic or non-robotic; and also includes scopes used in non-medical applications, such as, for example, borescopes, videoscopes, flexoscopes, and fiberscopes, whether robotic or non-robotic and includes any other scope disclosed herein.

The term "image capture device" as used herein also need not refer to devices that only have lenses or other light directing structure. Instead, for example, the image capture device could be any device that can capture and relay an image, including (i) relay lenses between the objective lens at the distal end of the scope and an eyepiece, (ii) fiber optics, (iii) charge coupled devices (CCD), (iv) complementary metal oxide semiconductor (CMOS) sensors. An image capture device may also be merely a chip for sensing light and generating electrical signals for communication corresponding to the sensed light or other technology for transmitting an image. The image capture device may have a viewing end—where the light is captured—and the conductive surface 302 may extend over a portion of the image capture element or may be applied away from the image capture element to other embodiments. Generally, the image capture device can be any device that can view objects, capture images and/or capture video.

Although one particular implementation of the optical coupler is described above, additional types of optical couplers may include some type of conductive material applied thereto. For example, U.S. Patent Application Publication No. 2012/0209074 filed Feb. 16, 2012, which is hereby incorporated herein by reference, discloses several variations on optical elements to which the conductive material may be applied.

Figure 5:
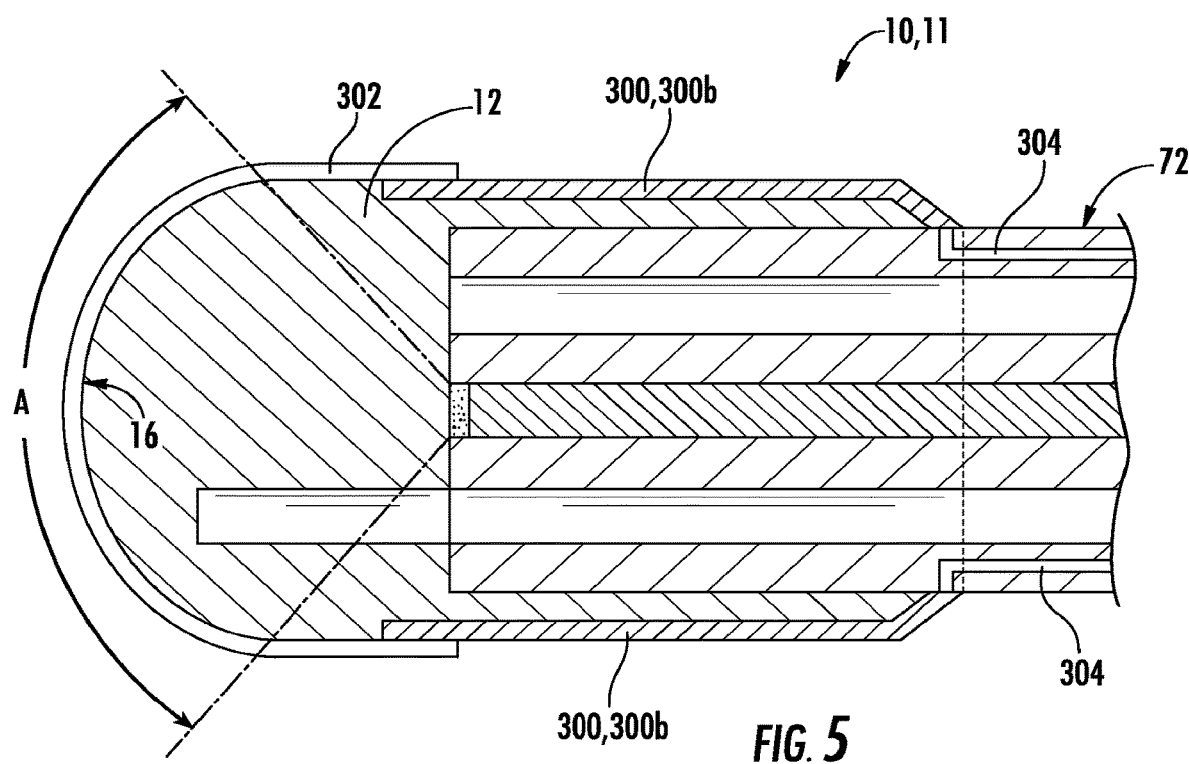
FIG. 5 shows a cross-sectional view of a device of another implementation of the present invention.

For example, FIG. 5 of the present disclosure shows another implementation of an optical element 10 attached to an endoscope 72. In FIG. 5, a portion of the outer surface 16 of the visualization section 12 is dome-shaped, and the portion of the outer surface of the visualization section that is dome-shaped is within the field of view A of the endoscope 72. For the dome-shape, the conductive material 302 may be required on an increased surface area with smoother transitions (as compared to FIGS. 1-4, if the entire dome is covered) or may be applied only within the field of view A.

Generally, the dome shape may improve imaging with an increased working space as organs can be pushed out of the field of view or this and other shapes may be utilized to optimize the field of view, the optical clarity, the conformance of the lens to targeted tissue or other matter. Other performance related reasons for adapting shapes of the optical element include a desire for light transmission, material adherence between shapes, navigation through a specific area, including a target lumen.

Figure 6:
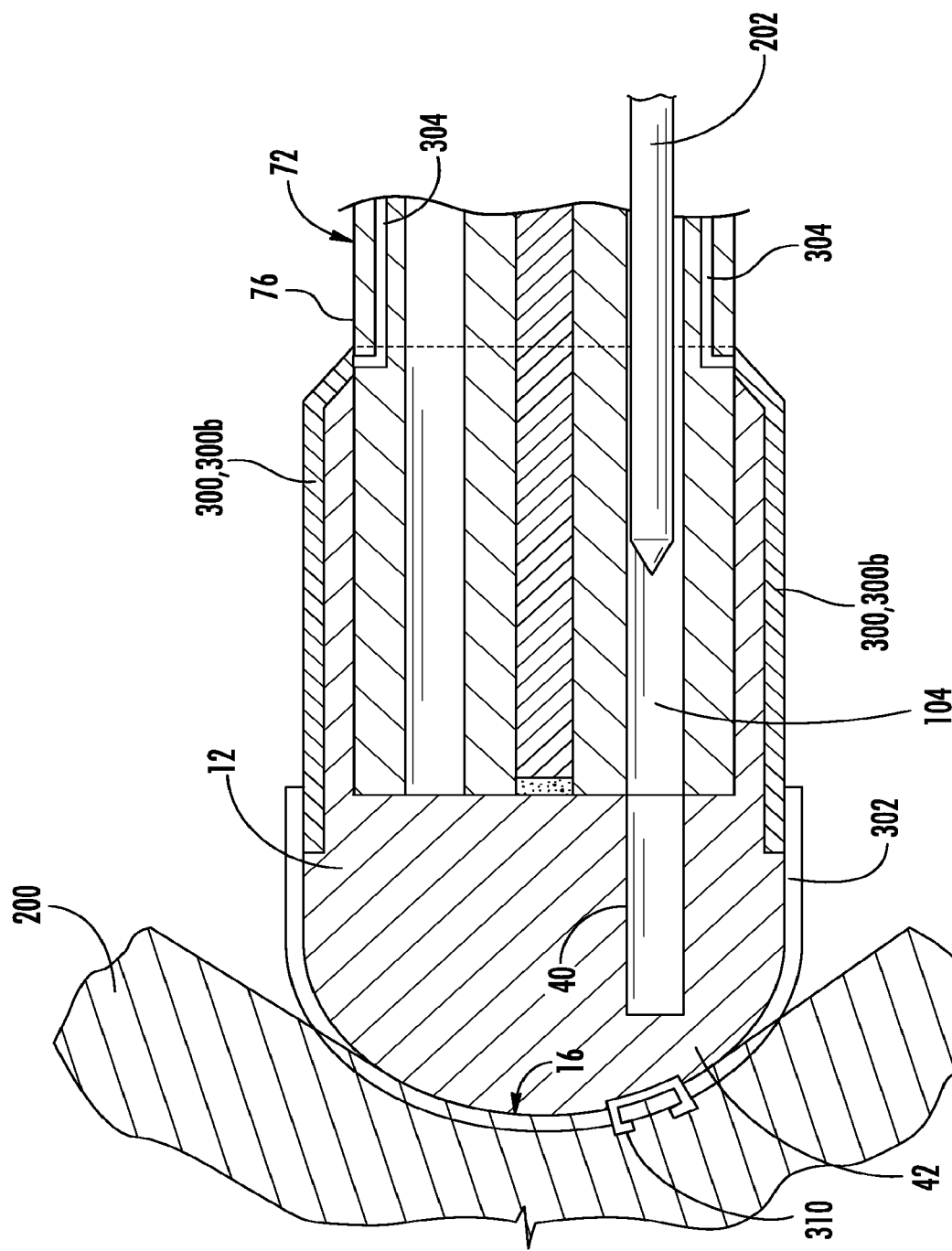
FIG. 6 shows another cross-sectional view of the device of FIG. 5.
Figure 7:
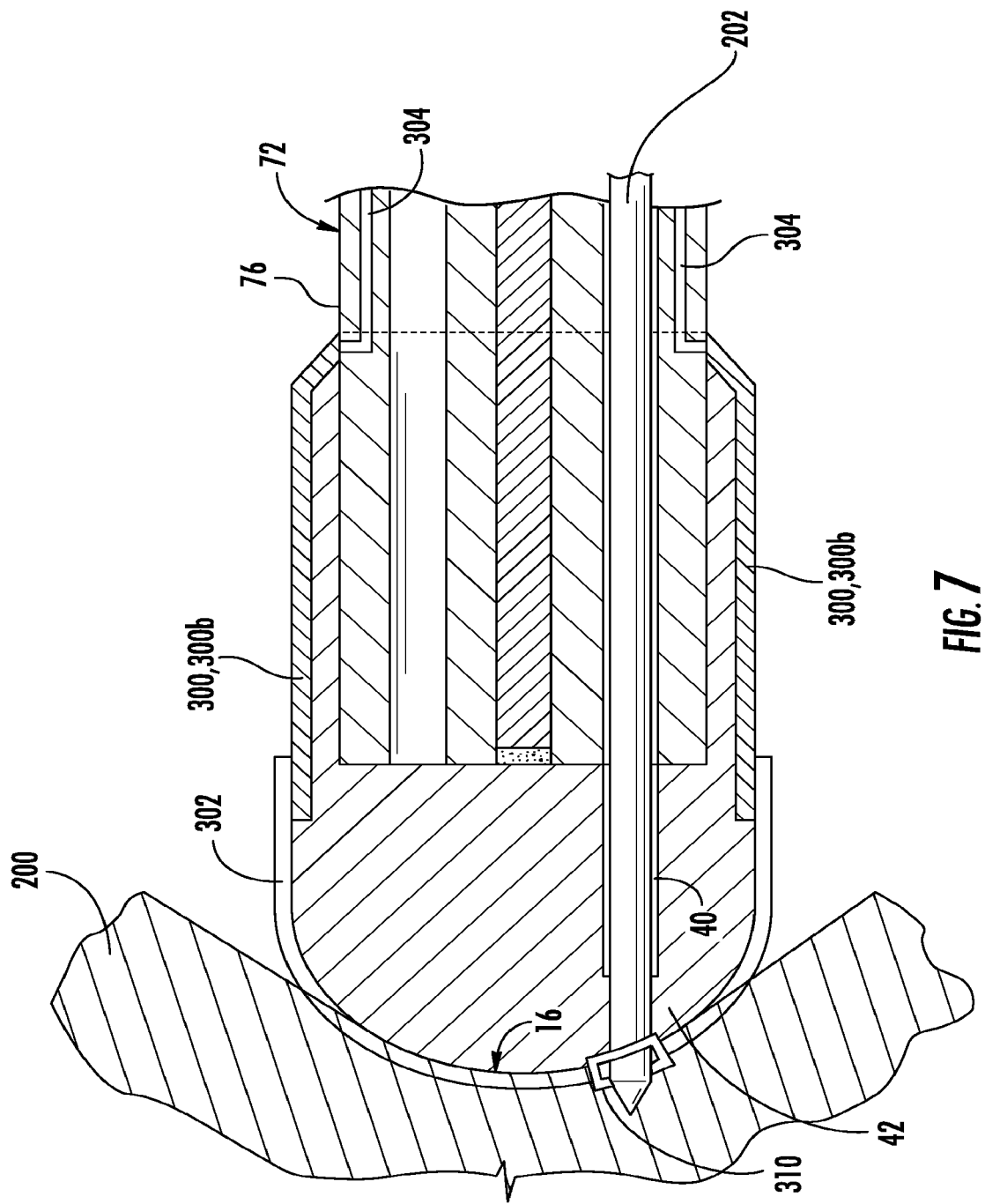
FIG. 7 shows another cross-sectional view of the device of FIG. 5.

As another example, FIG. 6 and FIG. 7 show an exemplary optical element 10 engaging a region of a body cavity 200. First the optical element 10 is placed in contact with a region of the body cavity 200. Then the physician can insert a medical instrument 202 (FIG. 6) in the third lumen 104 of the sheath 76 of the endoscope 72. The medical instrument is passed through the instrument receptacle 40 in the optical element and then the medical instrument 202 is pierced through a barrier section 42 and the outer surface 16 of the optical element 10 (FIG. 7 of present disclosure). A medical procedure can then be performed using the medical instrument on the region of the body cavity 200.

The barrier section 42 is a portion of the visualization section 12 that intervenes (prior to passage of the medical instrument 202) between the environment and the instrument receptacle 40. In one aspect, the barrier section may be coated with an insulating material 310 to prevent direct contact by the medical instrument 202 with the conductive material 302. The insulating material 310, for example, may extend from the outer surface 16 and be of the same or greater thickness than the layer of conductive material 302. Advantageously, the insulating material 310 may prevent a disruption of the conductivity of the conductive material 302, such as by a metal instrument causing a short to an electrically energized conductive material layer. Or, the insulating material may just be a more elastic, physical guard against damage by the medical instrument 202.

FIG. 8A shows a cross-sectional view of another implementation of an optical element attached to an endoscope 72. This implementation includes a biopsy forceps 61 placed through one of the endoscope 72's lumens 104 and through the optical element 10's instrument receptacle 40.

In FIG. 8A, the jaws of the biopsy forceps 61 are being opened. FIG. 8B is a cross-sectional view with the jaws of the biopsy forceps closed to take a biopsy sample from the body cavity 200. FIG. 8C is a cross-sectional view of the biopsy forceps being withdrawn after having taken the biopsy sample.

In the implementation of FIGS. 8A-C, the optical element 10 has a frusto-conical shape with the broader base extending distally. In this implementation, the conductive material 302 is relatively flat and can be easily applied to a relatively flat tissue surface. Also, the conductive material 302 may be in a layer with an opening that is surrounded by an insulating material 310. As described above, this can insulate against a short or damage by the biopsy forceps 61 to the conductive material. Also, the electrodes 300a and 300b may extend down the angled sides of the frusto-conical shape and may or may not be partially or fully insulated.

Figure 9A:
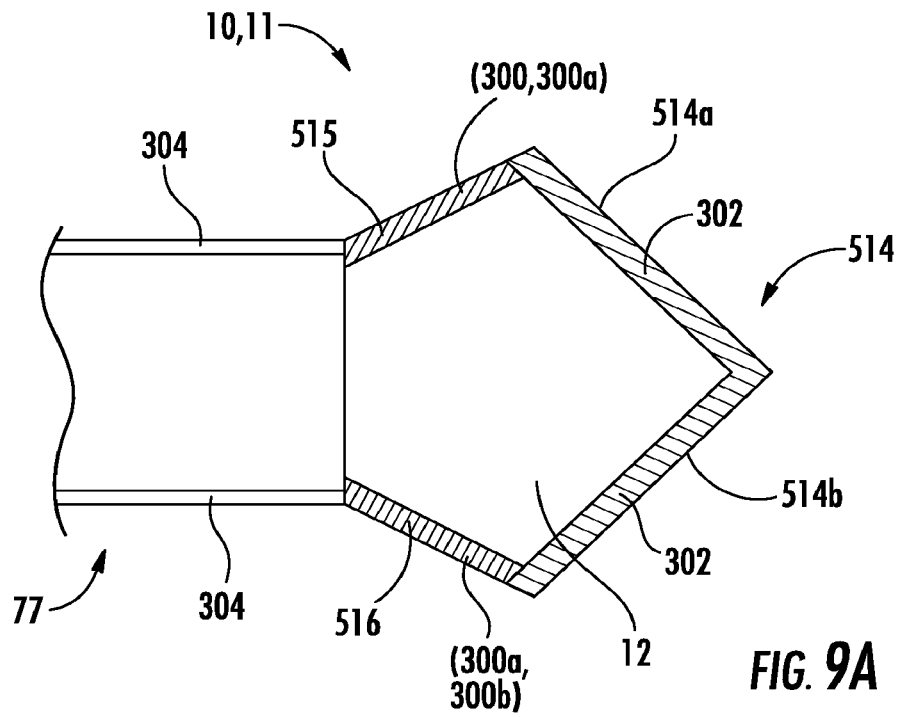
FIGS. 9A and 9B show a cross-sectional view of a device of another implementation of the present invention.
Figure 9B:
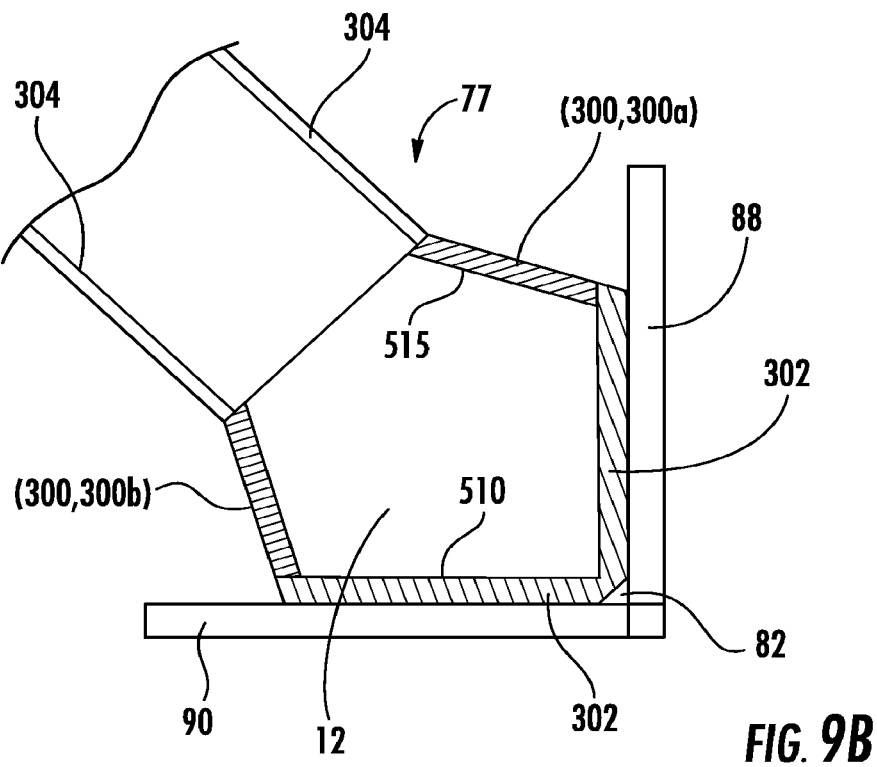

FIGS. 9A and 9B show another implementation of an optical element 10 with an angled outer surface 16. For example, the optical element 10 may be an optical coupler mounted to a borescope 77. The optical coupler 10 has a visualization section 12 that has a first outer boundary 515 and a second outer boundary 516. The first and second outer boundaries 515, 516 extend outwards from the borescope at an angle. An outer surface 514 of the coupler 10 is also angled, such that includes a first segment 514a and a second segment 514b. In this configuration, the conductive material layers 302 are similarly layered.

FIG. 9B shows the optical element 10 of FIG. 9A inspecting a weld lodged between two plates 88, 90. Advantageously, the electrodes 300 can deliver energy to the conductive layers 302 which may heat and/or alter the angled plates 88, 90, to, for example, repair the weld while the weld is being directly viewed by the operator.

Figure 10:
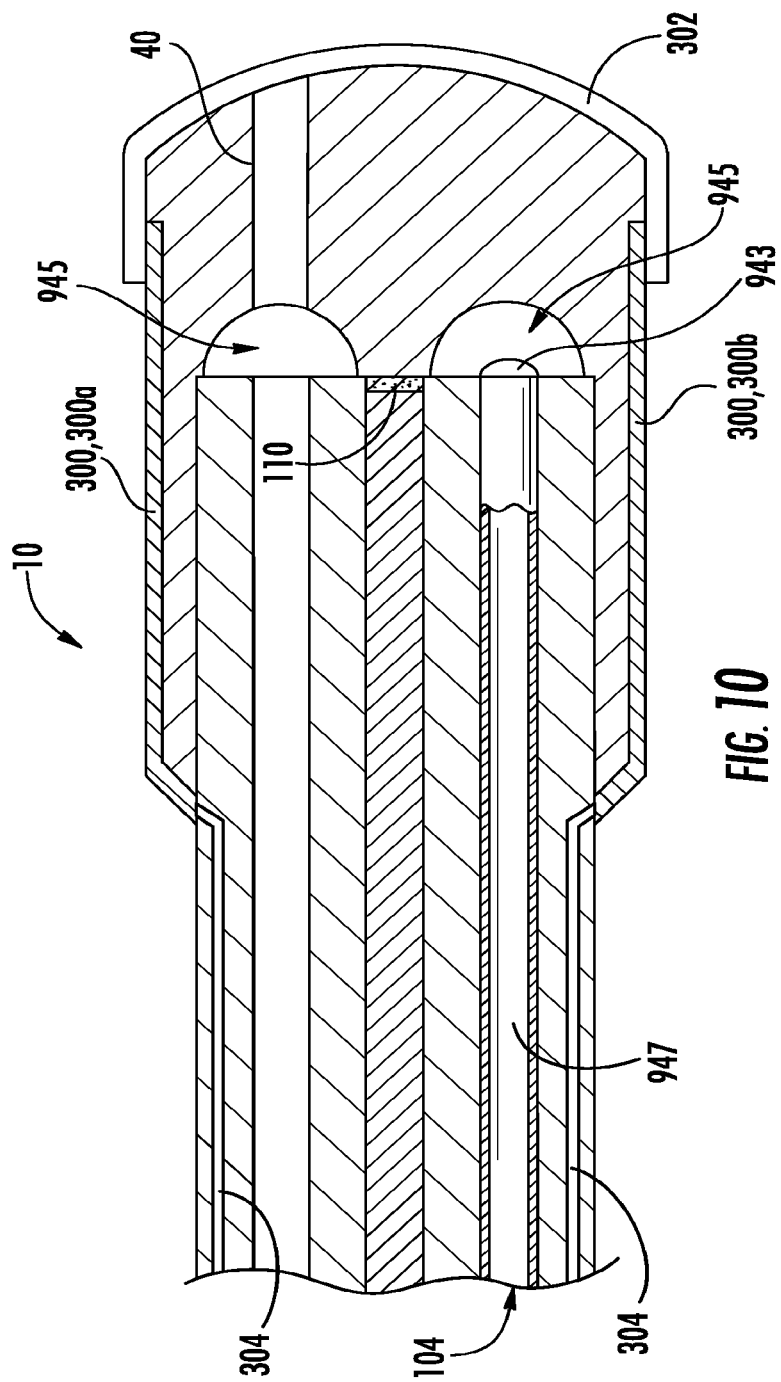
FIG. 10 shows a cross-sectional view of a device of another implementation of the present invention.

FIG. 10 shows an optical element 10 attached to an endoscope that has an auxiliary channel via the third lumen 104. A nozzle 943 is provided at the distal end of the auxiliary channel 104 for transmitting fluid, air or other matter. The optical coupler includes a chamber 945 extending around the long axis of the scope that can receive fluid 947 from the auxiliary fluid channel 104 and nozzle 943. This allows the fluid 947 to pass into and through the instrument receptacle 40 in the optical element 10. This channel can be used to transmit fluid, including water or saline to irrigate tissue or to rinse debris from the field of view or to clean the outer surface of the coupler, or to transmit drugs and other chemicals, and other matter, such as air, CO2, argon gas and other matter to effect targeted tissue or other matter. In FIG. 10, the conductive material 302 is applied in a layer similar to FIGS. 1-4. An opening may extend through the conductive material 302 for aspiration of the external environment as well as applying positive pressure to the instrument receptacle 40 when an instrument is deployed externally.

Figure 11A:
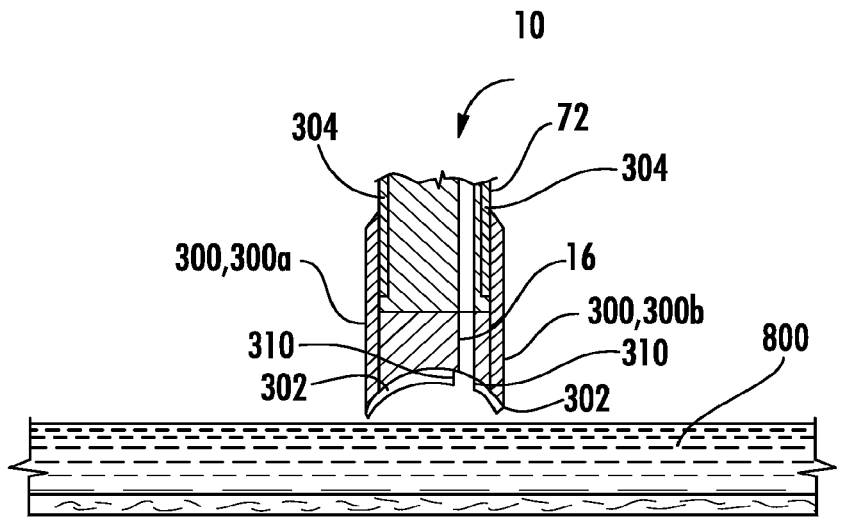
FIGS. 11A, 11B and 11C show a cross-sectional view of a device of another implementation of the present invention.
Figure 11B:
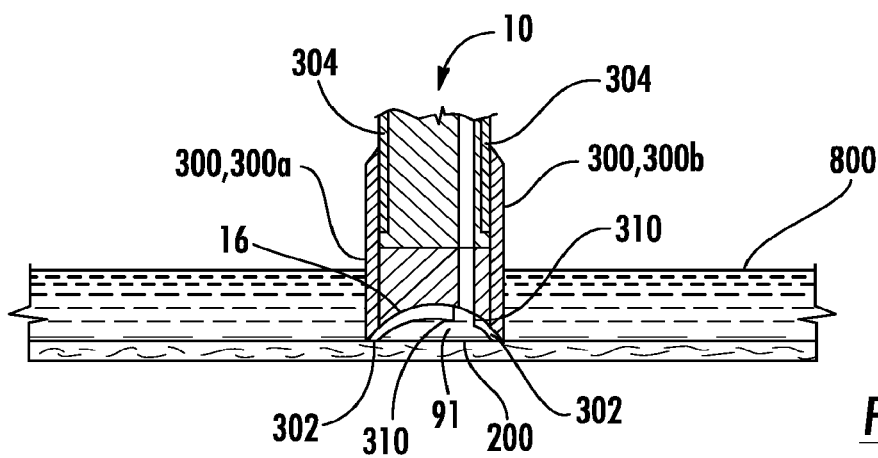
Figure 11C:
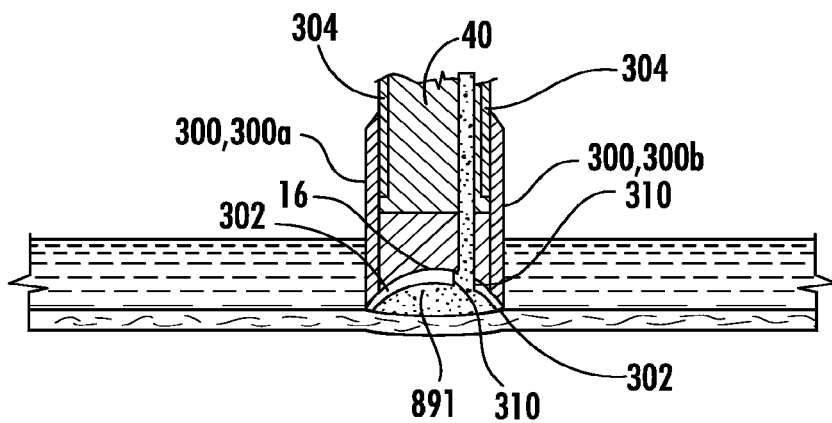

FIG. 11A of the present disclosure is a cross-sectional view of an optical element 10 having a concave outer surface 16 that is attached to an endoscope 72 approaching tissue covered in blood 800. FIG. 11B shows the optical element 10 pressed against a cavity in the tissue 200 and trapping opaque liquid 91. FIG. 11C shows fluid from the instrument receptacle 40 flushing the trapped opaque liquid 91. Advantageously, when the pressure of the introduced fluid exceeds the pressure exerted by the optical element 10 against body cavity 200, the fluid 891 will flush the trapped opaque liquid 91 from the area.

In FIGS. 11A and 11B, the conductive material 302 is applied in a concave layer, similar to the concave outer surface 16. The terminals 300 extend along the sides of the optical element 10 to make contact with ends of the concave conductive material 302.

Applications of the Device and Conductive Material

The conductive material 302 of the various implementations of the device 11 may be used to deliver many energy types and employed in many medical and non-medical applications. Examples of such energy types and applications are provided below for illustrative purposes and should not be considered limiting.

Figure 12:
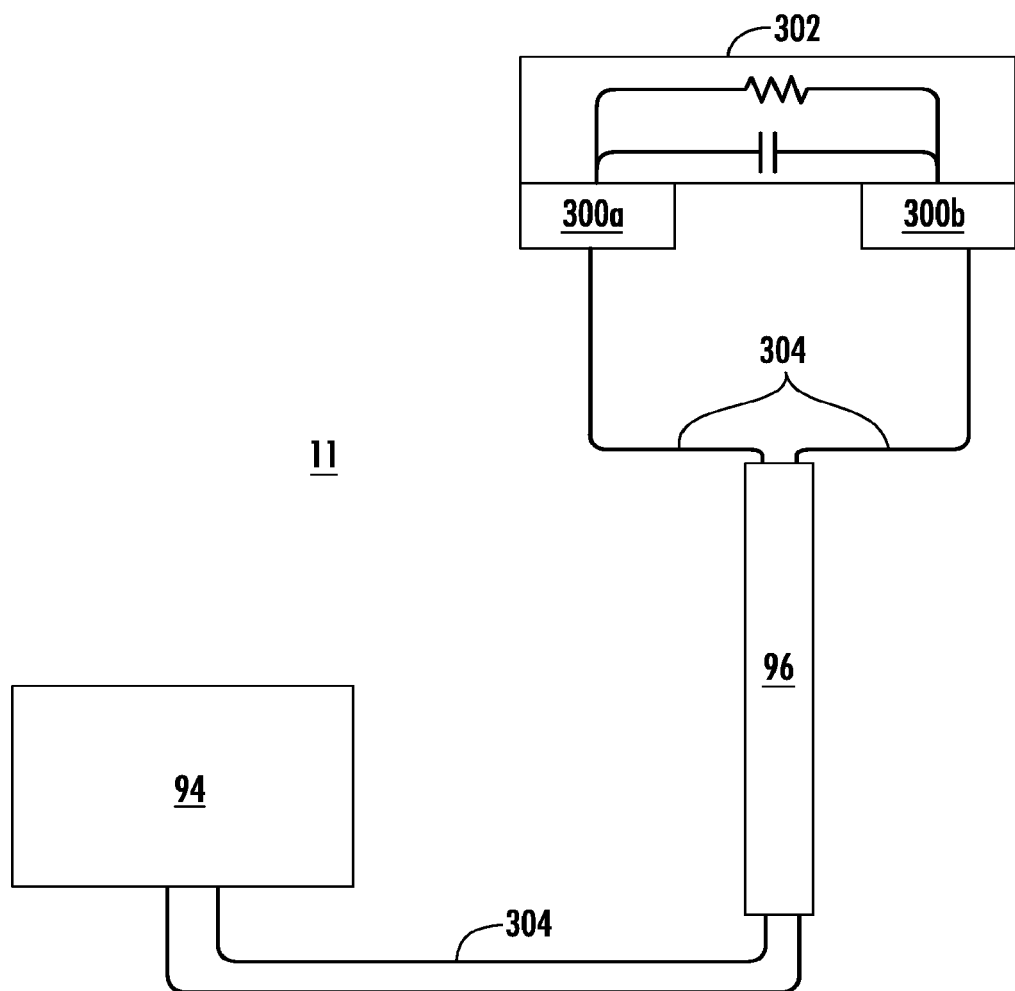
FIG. 12 shows a schematic diagram of a device of another implementation of the present invention.

As shown schematically in FIG. 12, the conductive material 302 is a resistor and/or capacitor attached via terminals 300a and 300b and a connector 304 and a cable 96 to a power source 94. The connector 304 may extend through the endoscope sheath 76, for example, and into the cable 96 attached to the endoscope's proximal end. Those connectors may connect to the power source 94 that may, for example, be one or more forms of energy for the alteration of tissue or other matter, including monopolar energy, bipolar energy, argon gas energy, coblation energy, plasma energy, thermal energy, microwave energy, ultrasound, focused ultrasound or other forms of energy, including the generation and transmission of multiple energy forms which can be transmitted across or through a conductive coating to alter tissue or matter, including for therapeutic effects. These can be delivered through direct current, alternating current, pulsed current and other variable forms of energy delivery.

There are many ways to deliver energy to the terminals 300 and the conductive material 302. The cable 96 can deliver power to the conductive material by way of the terminal 300, 300a, 300b. The cable can access the terminals by, for example, being adjacent to and outside of the scope or wrapped around the outside of the scope 72. Or, the cable 96 or connector 304 can be attached to an energy delivery catheter that is passed down the working channel (e.g., first lumen 100) of the scope and docks with the terminals. At its distal end, the energy delivery catheter may be connected to an electrical terminal in the working channel of the lens 110. The connectors 304 may also be embedded within the sheath 76 of the endoscope 72 and run parallel and close to the hollow instrument receptacle 40. The connectors may be comprised of flex circuits, one or more coatings, wires, conductive springs, inductive material for receiving and transmitting power, cables, or such other approaches for transmitting power from a power source toward a deliver point.

In another implementation, the electrical energy generator can comprise a signal generator such as: a function generator, an RF signal generator, a microwave signal generator, a pitch generator, an arbitrary waveform generator, a digital pattern generator or a frequency generator. An existing electrosurgical generator may be used with the advantage that it meets standards necessary for medical use. These generators may provide power to electronic devices that generate repeating or non-repeating electronic signals (in either the analog or digital domains). RF signal generators can range from a few kHz to 6 GHz. Microwave signal generators can cover a much wider frequency range, from less than 1 MHz to at least 20 GHz. Some models go as high as 70 GHz with a direct coaxial output, and up to hundreds of GHz when used with external waveguide source modules. Also FM and AM signal generators may be used.

The benefit of these different generators and others is they offer specific forms of power for targeted applications where one form of power has advantages over other forms. For example, when cutting and coagulating tissue, monopolar electricity typically can cut and coagulate through tissue more effectively than bipolar electrical energy. But monopolar energy requires the use of a grounding pad to avoid the arching of monopolar energy to unintentional areas. Hence, a grounding pad can be used with a monopolar application to affect tissue and prevent arching and subsequent electrical energy and burns to the patient with the monopolar energy. (The ground pad completes the circuit of the electrical energy through the patient.)

In contrast, bipolar electrical energy has a completed circuit in the device itself and therefore energy travels through and across the device, affecting tissue, but not arching through the body. With this approach, bipolar electrical energy can be very effective for creating lesions, sealing vessels and other applications involving targeted treatment of tissue. But, it tends to be less effective with cutting and coagulating through tissue as an alternative to a surgical knife because of the contained aspect of the bipolar electrical energy. Similarly, microwave energy may be used for certain types of ablation of tissue because of its unique tissue effect and bipolar energy may be used for other types of ablation. Other forms of energy, such as FM energy, may be used because the frequency does not excite certain collateral elements, such as nerve bundles.

A coablation generator can be used in the non-heat driven process of surgically disassociating soft tissue by using radiofrequency energy to excite the electrolytes in a conductive medium, such as saline solution, to create a precisely focused plasma field. Energized particles, or ions, in the plasma field can have sufficient energy to break, or dissociate, organic molecular bonds within soft tissue at relatively low temperatures, i.e., typically between 40° C. to 70° C. This enables coblation devices to volumetrically remove target tissue with minimal damage to surrounding tissue. Coblation can also provide hemostasis and tissue shrinkage capabilities. The amount of power delivered can be determined by intensity of the field and can be adjusted based on the local environmental condition.

Coblation may be used for temperature ranges typically up to 90° C.

An ultrasound generator is capable of generating acoustic waves having a frequency greater than approximately 20 kilohertz (20,000 hertz). The ultrasound waves may be conducted by the conductive material 302 to the tissue 200. Ultrasound can be absorbed by body tissues, especially ligaments, tendons, and fascia, or other matter.

Ultrasound devices can operate with frequencies typically from 20 KHz up to several GHz. Therapeutic ultrasound frequency used is typically between 0.7 to 3.3 MHz. Ultrasound energy or TENS energy may speed up the healing process by increasing blood flow in the treated area, decrease pain from the reduction of swelling and edema, and gently massage the muscles tendons and/or ligaments in the treated area.

Ultrasound may also non-invasively or invasively to ablate tumors or other tissue. This can accomplished using a technique known as High Intensity Focused Ultrasound (HIFU), also called focused ultrasound surgery (FUS surgery). This procedure uses generally lower frequencies than medical diagnostic ultrasound (250-2000 kHz). Other general conditions which ultrasound may be used for treatment include such as examples as: ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion.

The device 11 also allows a medical practitioner to perform among others, cauterization of tissue, vessel sealing, tissue dissection and re-sectioning, tissue shaping, tissue cutting and coagulation, tissue ablation, and instrument heating, all at the precise location that the practitioner is viewing. This at least partially addresses the problem of performing aspects of endoscopic surgery in the blind. It may also eliminate the need to exchange one device for another to apply energy to the tissue or matter or to deflect tissue or other matter or to engage in other manipulation while maintaining visualization.

More specific medical applications include, among others, application of energy to effect tissue in trauma cases, arthroscopic surgery, spine surgery, neurosurgery, shoulder surgery, lung tumor ablation, ablation of cancerous tissue with bladder cancer patients, cauterization or ablate uterine tissue for women's health issues (such as endometriosis). In these applications (and the other applications listed herein), the device can be used to contact tissue and then cauterize, ablate or shape the tissue (done with coblation energy for example in shoulder procedures), creating unique performance attributes by allowing the physician to see the change taking place to the tissue in real time through, for example, an optically clear lens and coating.

The device can also be used to heat an optically clear lens to prevent fogging during applications involving a laparoscope, borescope, videoscope or other optical capture technology.

To further elaborate on the medical applications, use of the device in diathermy applications is a useful area, whether achieved using short-wave radio frequency (range 1-100 MHz) or microwave energy (typically 915 MHz or 2.45 GHz). Diathermy used in surgery can comprise at least two types. Monopolar energy is where electrical current passes from one electrode near the tissue to be treated to the other fixed electrode elsewhere in the body. Usually this type of electrode is placed in a specific location on the body, such as contact with the buttocks or around the leg. Alternatively, bipolar energy can be used, where both electrodes are mounted in close proximity creating a closed electrical circuit on the device (in this case two separate conductive material portions 302 on the optical element 10) and electrical current passes only through or on the tissue being treated. An advantage of bipolar electrosurgery is that it prevents the flow of current through other tissues of the body and focuses only on the tissue in contact or close proximity to the electrodes. This is useful in, for example, microsurgery, laparoscopic surgery, cardiac procedures and in other procedures, including those with patients with cardiac pacemakers and other devices and conditions not suitable for use with other forms of energy.

Electrocauterization is the process of modifying tissue using heat conduction from electric current. The procedure is used to stop bleeding from small vessels (larger vessels can be ligated) or for cutting through soft tissue. High frequency alternating current is used in electrocautery in unipolar or bipolar fashion. It can be continuous waveform (to cut tissue) or intermittent type (to coagulate tissue). In unipolar type, the tissue to be coagulated/cut is to be contacted with small electrode, while the exit point of the circuit is large in surface area, as at the buttocks, to prevent electrical burns. Heat generated depends on size of contact area, power setting or frequency of current, duration of application, waveform. A constant waveform (generally) generates more heat than intermittent one because the frequency used in cutting the tissue is set higher than in coagulation mode. Bipolar electrocautery establishes circuit between two points to affect tissue or other matter.

As another option, the conductive layer 302 and device 11 may be used for thermal cautery in ranges of 50° C. through 100° C., or even in a range 50° C. through 70° C., or at a lesser temperature if advisable, with the application of a range of power, appropriate to the application. Advantageously, the ability to visualize as forms of energy are applied through the device allows for the precise delivery of energy, including changing the level of energy and resulting temperature, using power settings appropriate to the specific application, applying energy over a longer period of time to broaden coverage, applying energy across multiple electrodes for multiple effects, and the ability to stop the process with more confidence that the tissue or other matter has been satisfactorily transformed. (This advantage of course applies to other applications of the device 11—real time visual monitoring of energy application allows for more precision application.)

The optical element 10 may also be beneficial in non-medical applications. Implementations of the optical element can be attached to the distal end (objective lens) of a borescope or attached to micro or conventional video cameras, inspection scopes, or still cameras or any other visualization device that would benefit from improved visualization in fluid, debris and/or blood and delivery of energy. This allows improved viewing and the ability to make repairs inside pipes, holding tanks, containers, hydraulic lines and other circumstances where visualization may otherwise be impaired, including when fluid is opaque, such as petroleum products, sewerage, food products, paint. Biologic drug manufacturing, pharmaceutical products and other applications would benefit from this innovation, as well, eliminating the need to empty the pipes or containers (e.g., oil tanks) or open up the lines to inspect.

The size of the optical element or the amount of flexibility can be scaled for specific applications, for example, displacing large volumes of fluid when examining large areas. The shape of the optical element can be generally flat, convex (with varying levels of curvature), angled, sloped, stepped, or otherwise shaped for specific tasks. For example, the optical element may be shaped as a square, or as an angular shape to displace opaque fluids in the corners of a tank to inspect the seams. Examination of joints, welds, seams for corrosion, pipes, flexible and non-flexible tubular members, or cracks, surface aberrations, and other points of inspection and repair could be performed in pipes, lines, tubes, tunnels, and other passages.

An optical element could be used in conjunction with an image capture element and a robotic vehicle or a robotic arm to view remote locations. Optical components with working channels will allow devices to be passed through an optical element to make repairs using screws, adhesive patches, glues, chemicals, welding, soldering and other repair and modification applications. In embodiments, the optical element can be formed from materials that resist acid, alkalinity, high heat, or viscosity of the fluid being displaced by the optical element. In embodiments, the device could be a single-use disposable device or a reusable device.

Advantageously, implementations of the device 11 provide the ability to apply energy via the conductive material 302 in these varied non-medical applications. The energy provided to the viewed object may heat, alter or otherwise affect the object being viewed by the optical element 10.

Conductive Material Compositions

The conductive material 302 may have various compositions and be applied to the optical element 10 various ways. Examples of such compositions and applications are provided below for illustrative purposes and should not be considered limiting. For medical applications, the conductive material 302 preferable can withstand sterilization, such as by gamma irradiation, ethylene oxide, steam, or other forms of sterilization.

The electrically conductive/responsive coating can be applied in multiple configurations to create one or more electrodes. This electrode can be optically clear and of various thicknesses, including thickness of a half micron or less, and at much greater thicknesses, depending on the intended effect with tissue or other matter.

The conductive material can be at least partially transparent and can comprise for example, any member of the general class of materials known as transparent conductive oxides (TCOs), with titanium oxide ($TiO_2$) and aluminum-doped zinc oxide (AZO), being two examples. It could also involve applications of other conductive materials applied in a manner that permit visualization, such as silver and gold nanoparticles, and other conductive materials applied in a manner that allows for the conduction of energy and visualization.

Optical diffraction indexes for the visualization materials include materials with indexes of refraction that range from 1.3 to 2.3, depending on the application, the level of light transmission desired, the overall optical performance and other factors. A transparent conductive oxide may comprise transparent materials that possess bandgaps with energies corresponding to wavelengths which are shorter than the visible range of 380 nm to 750 nm. A film of a TCO can have a varying conductivity, for example, across points on the surface thereof. In one aspect, the film has no or substantially no pores, pinholes, and/or defects. In another aspect, the number and size of pores, pinholes, and/or defects in a layer do not adversely affect the performance of the layer in the device. The film thickness can range from less than 1 to about 3500 nm. In embodiments, different methods of fabrication and intended applications can lead to different thicknesses such as, for example, films about 10, 20, 30, 40, 50, 60, 70, 80, 100, 200, 300, 400, 500, 600, 700, 800, 900, 1000, 1300, and 1500 nm thick.

The transparent conductive film can be indium tin oxide, Al or Ga doped zinc oxide, Ta or Nb doped titanium oxide, F doped tin oxide, and their mixtures. The oxide layer can be formed by directly oxidizing an ultra-thin metal layer or by depositing an oxide. The TCO material can have polycrystalline, crystalline, or amorphous microstructures to affect the film properties, including for example, transmittance and conductivity, among other properties.

Biocompatible TCOs can also be used as the transparent conductive material. These include, for example, aluminum oxide ($Al_2O_3$), hydroxyapatite (HA), silicon dioxide ($SiO_2$) titanium carbide (TiC), titanium nitride (TiN), titanium dioxide ($TiO_2$), zirconium dioxide ($ZrO_2$). These materials may be n-doped with other metals such as aluminum, Al, copper, Cu, silver, Ag, gallium, Ga, magnesium, Mg, cadmium, Cd, indium, In, tin, Sn, scandium, Sc, yttrium, Y, cobalt, Co, manganese, Mn, chrome, Cr, and boron, B. p-Doping can be achieved with nitrogen, N, and phosphorus, P, among others.

$TiO_2$ can serve as a biocompatible material; it provides the possibility to coat substrates at temperatures ranging from room temperature to several hundreds of degrees centigrade. $TiO_2$ has multiple different polymorphic phases that can depend on the initial particle size, initial phase, dopant concentration, reaction atmosphere and annealing temperature. The $TiO_2$ films are commonly synthesized by many methods, including sol-gel, thermal spraying and physical vapor deposition.

Transparent conducting, aluminum doped zinc oxide thin films ($Al_xZn_yO_z$, ZnO:Al) contain a small amount (typically less than 5% by weight) of aluminum. The underlying substrate may have an influence on the grown structure and the opto-electronic properties of a film of the material. Even if the substrate is identical, the layer thickness (deposition time, position upon the substrate) itself influences the physical values of the deposited thin film.

A variation of the physical values from the grown thin films can also be reached by changing process parameters, as temperature or pressure, or by additions to the process gas, as oxygen or hydrogen. Commonly, zinc oxides are n-doped with aluminum. Alternatively, n-doping can be done with metals such as copper, Cu, silver, Ag, gallium, Ga, magnesium, Mg, cadmium, Cd, indium, In, tin, Sn, scandium, Sc, yttrium, Y, cobalt, Co, manganese, Mn, chrome, Cr, and boron, B. The p-Doping of ZnO can be achieved with nitrogen, N, and phosphorus, P.

Additionally, the incorporation of sub-wavelength metallic nanostructures in TCO can result in changes to the wavelength where the TCO becomes transparent. Embedded particles articles can also be used to control absorption and scattering at desired wavelengths. Other optical effects of the material can be influenced as well including absorption, scattering, light trapping or detrapping, filtering, light induced heating and others. The morphology of the particles (including size, shape, density, uniformity, conformity, separation, placement and random or periodic distribution) can be used to engineer these effects.

The substrate of the electrode of the invention can be of any suitable material on which the transparent electrode structure of this invention is applied. This can include another conductive material or a dielectric material. In one illustrative example, the optical element 10 serves as the substrate. Other substrates include, among others, glass, a semiconductor, an inorganic crystal, a rigid or flexible plastic material. Illustrative examples are silica ($SiO_2$), borosilicate (BK7), silicon (Si), lithium niobate ($LiNbO_3$), polyethylene naphthalate (PEN), polyethelene terephthalate (PET), among others.

Organic materials can also serve as the conductive material. These include carbon nanotube networks and graphene, which can be fabricated to be highly transparent to infrared light, along with networks of polymers such as poly(3,4-ethylenedioxythiophene) and its derivatives.

Polymers can also serve as the conductive material. For example, conductive polymers such as derivatives of polyacetylene, polyaniline, polypyrrole or polythiophenes. poly (3,4-ethylenedioxythiophene) (PEDOT), and PEDOT: poly (styrene sulfonate) PSS. Additionally, Poly(4,4-dioctylcyclopentadithiophene) doped with iodine or 2,3-dichloro-5,6-dicyano-1,4-benzoquinone (DDQ) can be used. Other polymers with n or p type dopants can also be used.

Conductive material films can be deposited on a substrate through various deposition methods, including metal organic chemical vapor deposition (MOCVD), metal organic molecular beam deposition (MOMBD), spray pyrolysis, and pulsed laser deposition, dip coating, painting, gluing or other applications suitable for appropriately adhering the conductive materials to the given substrate for the particular application. Fabrication techniques of TCOs include magnetron sputtering of the film, sol gel technology, electro deposition, vapor phase deposition, magnetron DC sputtering, magnetron RF sputtering or a combination of both the sputter deposition methods, ultrasonic delivery and welding. Moreover, high quality deposition methods using thermal plasmas, (low pressure (LP), metal organic (MO), plasma enhanced (PE)) chemical vapor deposition (CVD), electron beam evaporation, pulsed laser deposition and atomic layer deposition (ALD) can be applied, among others.

A thin film, such as ALD, only a few nanometers thick can be flexible and thus less prone to cracking and formation and spreading of detrimental particles inside the human body or insider the given non-medical inspection site. Also, low and high protein binding affinity coatings can be deposited by ALD. They are especially useful in diagnostics and in the preparative field, as well as for surface coatings that resist bacterial growth.

Pre and post deposition processing such as processing with an oxygen plasma and thermal treatment can be combined to obtain improved conductive material characteristics. The oxygen plasma might be preferable for when the substrate, or conductive material would be affected by the high temperatures. The conductive material film can have a wide range of material properties depending on variations in process parameters. For example, varying the process parameters can result in a wide range of conductivity properties and morphology of the film.

The term "connector" as used herein should be construed broadly to mean any structure that enables electrical or other energy communication to the conductive coating. The term "connector" can refer to a permanent connection (solder, gluing, twisted wires, a conductive path with a conductive coating) or exchangeable connectors, like a plug and harness assembly, or other way of transmitting energy from a power source towards the conductive coating. It need not be a physical connection all the way through to the coating. It could, for example, connect via electromagnetic field—such as by inductance. The term "connector" may also include structure and/or function that allows, mediates, enhances or otherwise facilitates a connection. A particular type of connector is a terminal that may be, for example, an area of conductive material provided for or capable of electrical coupling with a power source. A terminal, for example, may be a conductive metal layer deposed on a surface and shaped for contact with an end of a wire on an energy supply catheter.

A "connector area" is an area where the connector can be attached, mounted, coated, glued, affixed, adhered, layers, overlapped or can otherwise communicate energy to the conductive coating.

A number of aspects of the systems, devices and methods have been described. Nevertheless, it will be understood that various modifications may be made without departing from the spirit and scope of the disclosure. Accordingly, other aspects are within the scope of the following claims.

What is claimed is:

1. A device for use with an endoscope having an optical lens, the device comprising:
   an optical coupler having a distal end, a proximal end, a visualization section at the distal end, and an attachment section at the proximal end for attachment to the endoscope, wherein the visualization section is configured to cover at least a portion of the optical lens of the endoscope and being capable of transmitting an optical image through the optical coupler;
   an electrically conductive coating disposed on at least a portion of the distal end of the optical coupler, wherein the electrically conductive coating is at least partially transparent;
   at least one connector capable of providing energy to the electrically conductive coating; and
   a working channel extension within the optical coupler for receiving an instrument, fluid or gas, wherein the working channel extension extends from the endoscope through the visualization section to an outer surface of the visualization section.

2. The device of claim 1, wherein the electrically conductive coating includes a conductive oxide.

3. The device of claim 2, wherein the conductive oxide is selected from the group consisting of a titanium conductive oxide and an aluminum conductive oxide.

4. The device of claim 1, wherein the electrically conductive coating comprises an electrode configured to delivery energy to tissue adjacent to, or in contact with, the optical coupler.

5. The device of claim 1, wherein the electrically conductive coating is configured to generate and transmit thermal energy to tissue disposed adjacent to, or in contact with, the optical coupler.

6. The device of claim 1, wherein the working channel extension has a proximal end portion configured to couple to a distal end portion of a working channel in the endoscope.

7. The device of claim 6, wherein the proximal end portion of the working channel extension is configured to contact a portion of the surface of the endoscope adjacent to the distal end portion of the working channel of the endoscope.

8. The device of claim 7, wherein the working channel extension has a distal opening disposed within the visualization section and spaced proximally from at least one portion of the electrically conductive coating.

9. An endoscope assembly comprising:
   an endoscope having an optical lens, an internal working channel and a distal end portion, and
   an optical coupler comprising:
      a visualization section at a distal end of the optical coupler;
      an attachment section at a proximal end of the optical coupler and configured for attachment to the distal end portion of the endoscope, wherein the visualization section is configured to cover at least a portion of the optical lens of the endoscope and being capable of transmitting an optical image through the optical coupler;
      an electrically conductive coating disposed on at least a portion of the distal end of the optical coupler, wherein the electrically conductive coating is at least partially transparent; and
      at least one connector capable of providing energy to the electrically conductive coating; and
      a working channel extension within the optical coupler for receiving an instrument, fluid or gas, wherein the working channel extension extends from the internal working channel of the endoscope through the visualization section to an outer surface of the visualization section.

10. The endoscope assembly of claim 9, wherein the electrically conductive coating includes a conductive oxide.

11. The device of claim 10, wherein the conductive oxide is selected from the group consisting of a titanium conductive oxide and an aluminum conductive oxide.

12. The device of claim 9, wherein the electrically conductive coating comprises an electrode configured to delivery energy to tissue adjacent to, or in contact with, the optical coupler.

13. The device of claim 9, wherein the electrically conductive coating is configured to generate and transmit thermal energy to tissue disposed adjacent to, or in contact with, the optical coupler.

14. The device of claim 9, wherein the working channel extension has a proximal end portion configured to couple to a distal end portion of the internal working channel in the endoscope.

15. The device of claim 14, wherein the proximal end portion of the working channel extension is configured to contact a portion of the surface of the endoscope adjacent to the distal end portion of the internal working channel of the endoscope.

16. The device of claim 14, wherein the working channel extension has a distal opening disposed within the visualization section and spaced proximally from at least one portion of the electrically conductive coating.

\* \* \* \* \*